United States Patent
Yu et al.

(10) Patent No.: US 10,585,151 B2
(45) Date of Patent: Mar. 10, 2020

(54) SQUID SENSOR MODULE AND MAGNETOENCEPHALOGRAPHY MEASURING APPARATUS

(71) Applicant: KOREA RESEARCH INSTITUTE OF STANDARDS AND SCIENCE, Daejeon (KR)

(72) Inventors: Kwon-Kyu Yu, Daejeon (KR); Yong-Ho Lee, Daejeon (KR); Kiwoong Kim, Daejeon (KR); Jin-Mok Kim, Daejeon (KR); Hyukchan Kwon, Daejeon (KR); Sang-Kil Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 1002 days.

(21) Appl. No.: 15/097,912

(22) Filed: Apr. 13, 2016

(65) Prior Publication Data
US 2016/0223622 A1    Aug. 4, 2016

Related U.S. Application Data

(63) Continuation of application No. PCT/KR2014/009612, filed on Oct. 14, 2014.

(30) Foreign Application Priority Data

Oct. 24, 2013    (KR) .................. 10-2013-0126944

(51) Int. Cl.
*A61B 5/00* (2006.01)
*G01R 33/035* (2006.01)
(Continued)

(52) U.S. Cl.
CPC ...... *G01R 33/0354* (2013.01); *A61B 5/04008* (2013.01); *A61B 5/6803* (2013.01);
(Continued)

(58) Field of Classification Search
None
See application file for complete search history.

(56) References Cited

U.S. PATENT DOCUMENTS 5,666,052 A * 9/1997 Sata .................. G01R 33/0354
324/248
7,729,740 B2   6/2010 Kraus, Jr. et al.

FOREIGN PATENT DOCUMENTS

JP    2010-046350 A    3/2010
JP    5 101 433 B2    12/2012
(Continued)

OTHER PUBLICATIONS

International Search Report for Application No. PCT/KR2014/009612 dated Nov. 27, 2014.
(Continued)

*Primary Examiner* — Joel F Brutus
(74) *Attorney, Agent, or Firm* — Jenkins, Wilson, Taylor & Hunt P.A.

(57) ABSTRACT

Superconducting quantum interference device (SQUID) sensor module and a magnetoencephalography (MEG) measuring apparatus. The SQUID sensor module includes a fixed block having one end fixed to the sensor-mounted helmet, a bobbin having one end combined with the other end of the fixed block and having a groove in which a pick-up coil is wound, a bobbin fixing or attachment structure or material fixed to the other end of the fixed block via a through-hole formed in the center of the bobbin, a SQUID printed circuit board (PCB) disposed one an upper side surface of the bobbin and including a SQUID sensor, and a signal line connection PCB inserted into an outer circumferential surface of the fixed block and adapted to transmit a signal detected in the SQUID sensor to an external circuit.

7 Claims, 16 Drawing Sheets

(51) Int. Cl.
*A61B 5/04* (2006.01)
*G01R 33/00* (2006.01)
*G01R 33/022* (2006.01)

(52) U.S. Cl.
CPC ....... *G01R 33/0017* (2013.01); *G01R 33/022* (2013.01); *G01R 33/035* (2013.01); *A61B 2562/0223* (2013.01); *A61B 2562/166* (2013.01); *A61B 2562/222* (2013.01)

(56) References Cited

FOREIGN PATENT DOCUMENTS

| KR | 10-2000-0031387 A | 6/2000 |
| KR | 10-2011-0076150 A | 7/2011 |
| KR | 10-1081482 B1 | 11/2011 |
| KR | 10-1243318 B1 | 3/2013 |

OTHER PUBLICATIONS

Korean Office Action for Application No. 10-2013-0126944 dated Sep. 23, 2014.
Korean Grant of Patent for Application No. 10-2013-0126944 dated Mar. 19, 2015.
IPRP and Written Opinion for Application No. PCT/KR2014/009612 dated Apr. 26, 2016.

\* cited by examiner

SQUID SENSOR MODULE AND MAGNETOENCEPHALOGRAPHY MEASURING APPARATUS

CROSS-REFERENCE TO RELATED APPLICATIONS

This application is a continuation of and claims priority to PCT/KR2014/009612 filed on Oct. 14, 2014, which claims priority to Korea Patent Application No. 10-2013-0126944 filed on Oct. 24, 2013, the entireties of which are both hereby incorporated by reference.

TECHNICAL FIELD

The present disclosure relates to SQUID sensor modules and, more particularly, to a SQUID sensor module in which a pick-up coil and a SQUID sensor are combined into one body.

BACKGROUND

A person's brain has many brain nerve cells, and a magnetoencephalography (hereinafter referred to as "MEG") signal is generated by ionic electrical activity of the brain nerve cells. If an MEG signal is measured, medical applications such as diagnosis of brain functions, localization of an epilepsy developing location, and cognitive function diagnosis are made possible. However, an MEG signal generated from a brain is a very weak signal of tens to hundreds of femto-Tesla (fT). A high-sensitivity magnetic sensor and technical development capable of effectively shielding earth's magnetic field and environmental noise are required to detect such a weak signal with a high signal-to-noise ratio (SNR).

A superconducting quantum interference device (hereinafter referred to as "SQUID") sensor using a superconductor is a magnetic sensor having very high sensitivity and is necessarily used in an MEG signal measuring system. A SQUID sensor needs to be connected to a pick-up coil to measure a magnetic signal with the SQUID sensor. According to types of pick-up coils, SQUID sensors are classified into a magnetometer adapted to measure a magnetic field value and a gradiometer adapted to measure spatial differential of a magnetic field.

A method for removing environmental magnetic noise includes a method for fabricating a signal pick-up coil in the form of a gradiometer and a method for mounting a magnetically shielded room (MSR) using a metal having high permeability and a metal having high electrical conductivity. Moreover, the environmental magnetic noise may be additionally removed through the procedure of processing a measured signal.

When a pick-up coil is fabricated in the form of a gradiometer, a first-order gradiometer is generally introduced. In this case, spatially non-uniform noise may not be removed effectively or a reference channel may reduce a signal to cause SNR reduction.

A SQUID sensor module may include a SQUID sensor and a pick-up coil. Preferably, the pick-up coil is disposed adjacent to a measurement target such that the SQUID sensor module measures a biomagnetic signal. On the other hand, an MEG measuring apparatus includes a Dewar including a helmet-shaped sensor-mounted helmet and a plurality of SQUID sensor modules disposed around the sensor-mounted helmet. A structure of the SQUID sensor module has an effect on measurement sensitivity of a biomagnetic signal and consumption efficiency of a refrigerant. Accordingly, there is a requirement for a SQUID sensor module with an improved structure.

Magnetic shielding using a magnetically shielded room may effectively shield a magnetic field but requires a long fabrication time and a wide fabrication space. In addition, since magnetic shielding must use Permalloy which has high permeability and a metal having high electrical conductivity, much cost is required. To overcome these disadvantages, various studies have been conducted on magnetic shielding using Meissner effect that is a characteristic where a magnetic field cannot penetrate a superconductor under a superconducting state. Superconducting shield has constant shielding performance according to a frequency and is an ideally perfect shielding method.

When a superconductor is implemented in the form of a helmet using superconducting shielding characteristics, a superconducting helmet may suppress a noise from a low frequency to a high frequency due to superconducting shielding effect in the superconducting helmet. In particular, when a conventional magnetically shielded room is used, many high-priced Permalloys must be used to obtain a high shielding factor in a low-frequency region of 0.1 Hz or less. However, in case of superconducting shield, a high shielding factor may be obtained even in the low-frequency region of 0.1 Hz or less.

According to superconducting shielding theory, when a magnetic signal source $M_{source}$ is disposed at a position spaced apart by a distance "a" in a direction perpendicular to a superconductor plane, current flowing to a superconducting shielding material surface, a virtual magnetic signal source $M_{image}$ of the same size but an opposite direction is likely to exist opposite to the magnetic signal source $M_{source}$. Therefore, theoretically, a gradiometer spaced part from a superconductor surface by the distance "a" operates the same as a primary gradiometer whose base line is "2a", which was proved by the Los Alamos National Laboratory (LANL) study group.

Thus, when a superconductor is fabricated in the form of a helmet, magnetic shielding may be achieved in a superconducting helmet. According to depth of a signal source desired to be measured, spaced distance between a superconductor material surface and a pick-up coil may be adjusted to determine length of a base line. In addition, the superconducting shield may provide a constant shielding effect according to a frequency. The LANL study group announced the effectiveness of superconducting shield by manufacturing an MEG apparatus in the form of a shielding helmet directly cooled with liquid helium and measuring a shielding factor depending on each position of a gradiometer in the helmet and a somatosensory signal.

However, according to a result of the LANL study group, a signal-to-noise ratio of a gradiometer disposed at the edge of an MEG helmet was lower than when superconducting shielding is not performed. The reduction in the signal-to-noise ratio of the gradiometer disposed at the edge of the MEG helmet is caused by the fact that density of a magnetic-force line increased at the edge of the helmet. An MEG signal was actually measured depending on whether superconducting shielding is performed. When the superconducting shielding was performed, a somatosensory signal near a vertex was measured to have a high signal-to-noise ratio whereas an evoked signal for an auditory cortex and a visual cortex reacting at left and right temporal regions and an occipital region had a very low signal-to-noise ratio. In particular, when superconducting shielding was performed, a cardiac magnetic signal and an interest vibration noise of a measurement person were measured to be very high and great at the edge of a superconducting shielding helmet. The significant increase in external noise intensity is caused by magnetic field focusing effect at the edge of the superconducting shielding helmet.

Referring to U.S. Pat. No. 7,729,740, to overcome the above problem, the LANL study group mounted a reference magnetometer for measuring only an environmental magnetic noise outside a superconducting shielding helmet and applied an adaptive filter to remove the noise. However, when the adaptive filter is used, the inside of the superconducting shield and an external nose must have the same frequency and the same frequency element. In addition, when the noise element is much greater than a signal element desired to be measured, the application of the adaptive filter is not effective. In particular, a magnetic signal generated from a person's heart is detected by a magnetometer inside the helmet but is not often detected by a reference magnetometer.

Accordingly, there is a need for a novel superconducting shielding structure to improve a structure of a SQUID sensor module and a shielding effect at the edge of a helmet.

SUMMARY

Example embodiments of the present disclosure provide an economical magnetoencephalography (MEG) measuring apparatus that measures an MEG signal having a superior signal-to-noise ratio (SNR) by using a SQUID sensor module with improved spatial availability.

Example embodiments of the present disclosure provide a SQUID sensor module having a compact structure combined in an integral type.

A superconducting quantum interference device (SQUID) sensor module according to an example embodiment of the present disclosure includes: a fixed block having one end fixed to a supporting part; a bobbin having one end combined with the other end of the fixed block and a groove in which a pick-up coil is wound; a bobbin fixing or attaching structure fixed to the other end of the fixed block via a through-hole formed in the center of the bobbin; a SQUID printed circuit board (PCB) disposed on an upper side surface of the bobbin and including a SQUID sensor; and a signal line connection PCB inserted into an outer circumferential surface of the fixed block and adapted to transmit a signal detected in the SQUID sensor to an external circuit.

In an example embodiment, the signal line connection PCB may include a first connector. The SQUID PCB may include a second connector, and the first connector and the second connector may be electrically connected to each other.

In an example embodiment, the fixed block may include: a fixed block protruding portion having a disc shape and combined with a groove or a through-hole formed at the supporting part; a fixed block threshold portion having a disc shape, continuously connected to the fixed block protruding portion, and having a flat side surface having a larger diameter than the fixed block protruding portion; a fixed block body portion having a disc shape, continuously connected to the fixed block threshold portion, and having a flat side surface having a smaller diameter than the fixed block threshold portion; and a fixed block extending portion having a diameter equal to that of the fixed block body portion and having a flat side surface. The flat side surface of the fixed block threshold portion and the flat side surface of the fixed block body portion may be connected to each other. One side surface of the fixed block body portion and one side surface of the fixed block extending portion may be parallel to each other. A vertical distance between a central shaft and one side surface of the fixed block extending portion may be smaller than a vertical distance between the central shaft and one side surface of the fixed block body portion.

In an example embodiment, the bobbin may include: a first flat portion having a first vertical distance from a central shaft and formed on an upper side surface; and a second flat portion having a second vertical distance greater than the first vertical distance and formed on a lower side surface.

In an example embodiment, the SQUID sensor module may further include a connection line electrically connecting the pick-up coil and the SQUID sensor to each other. Opposite ends of the pick-up coil may be fixed to the second flat portion, and the connection line may electrically connect a conductive pad of the SQUID sensor and the opposite ends of the pick-up coil to each other.

In an example embodiment, the signal line connection PCB may be in the form of a washer having a through-hole formed therein. One side surface of the through-hole may be a plane to prevent a rotational motion when the signal line connection PCB is combined with an outer circumferential surface of the fixed block.

In an example embodiment, the pick-up coil may be a first-order gradiometer or a magnetometer.

A magnetoencephalography (MEG) measuring apparatus according to an example embodiment of the present disclosure includes: an inner container storing a liquid refrigerant and including an inner helmet; an outer container including an outer helmet disposed to cover the inner helmet; a sensor-mounted helmet disposed inside the inner container; and a superconducting quantum interference device (SQUID) sensor module mounted on the sensor-mounted helmet. The SQUID sensor module may include: a fixed block having one end fixed to the sensor-mounted helmet; a bobbin having one end combined with the other end of the fixed block and having a groove in which a pick-up coil is wound; a bobbin fixing or attachment structure or material fixed to the other end of the fixed block via a through-hole formed in the center of the bobbin; a SQUID printed circuit board (PCB) disposed one an upper side surface of the bobbin and including a SQUID sensor; and a signal line connection PCB inserted into an outer circumferential surface of the fixed block and adapted to transmit a signal detected in the SQUID sensor to an external circuit.

In an example embodiment, the MEG measuring apparatus may further include a superconducting helmet disposed on the sensor-mounted helmet. The sensor-mounted helmet may be disposed between the superconducting helmet and the inner helmet, and the SQUID sensor module may be disposed between the inner helmet and the sensor-mounted helmet.

In an example embodiment, the pick-up coil may be a magnetometer.

A magnetoencephalography (MEG) measuring apparatus according to an example embodiment of the present disclosure includes: an inner container storing a liquid refrigerant and including an inner helmet; an outer container including an outer helmet disposed to cover the inner helmet; a sensor-mounted helmet disposed in a space between the inner helmet and the outer helmet; and a superconducting quantum interference device (SQUID) sensor module disposed in a space between the sensor-mounted helmet and the outer helmet and mounted on the sensor-mounted helmet. The SQUID sensor module may include: a fixed block having one end fixed to the sensor-mounted helmet; a bobbin having one end combined with the other end of the fixed block and having a groove in which a pick-up coil is wound; a bobbin fixing or attachment structure or material fixed to the other end of the fixed block via a through-hole formed in the center of the bobbin; a SQUID printed circuit board (PCB) disposed one an upper side surface of the bobbin and including a SQUID sensor; and a signal line connection PCB inserted into an outer circumferential surface of the fixed block and adapted to transmit a signal detected in the SQUID sensor to an external circuit.

In an example embodiment, the MEG measuring apparatus may further include a superconducting helmet disposed in a space between the inner helmet and the sensor-mounted helmet.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
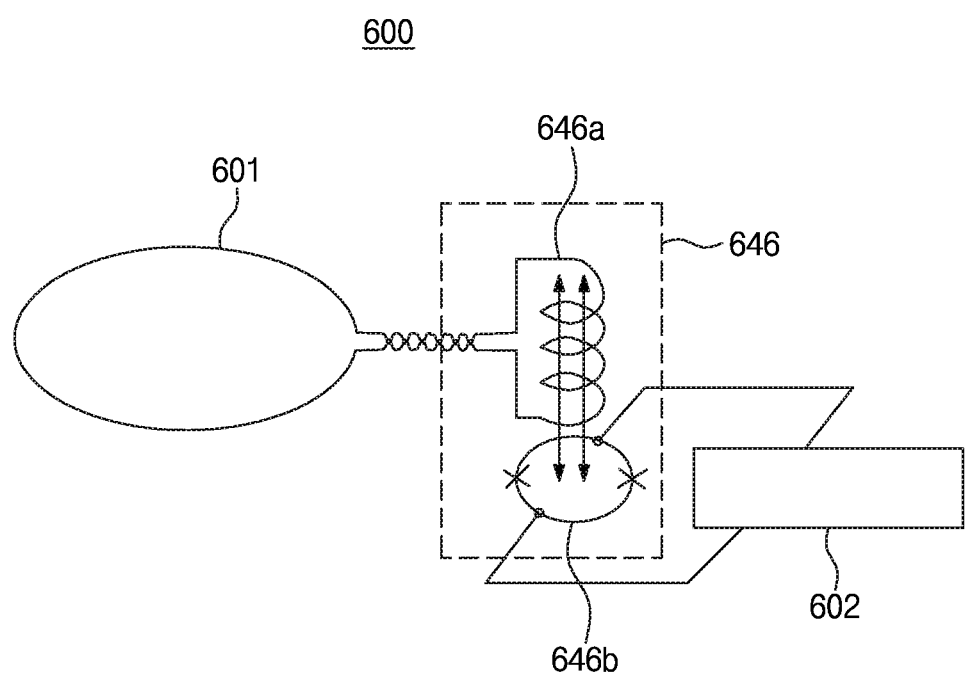
FIG. 1 is a conceptual diagram of a SQUID sensor module according to an example embodiment of the present disclosure.

Example embodiments will now be described more fully with reference to the accompanying drawings, in which some example embodiments are shown. Example embodiments may, however, be embodied in many different forms and should not be construed as being limited to the embodiments set forth herein; rather, these example embodiments are provided so that this disclosure will be thorough and complete, and will fully convey the scope of example embodiments of inventive concepts to those of ordinary skill in the art. In the drawings, the thicknesses of layers and regions are exaggerated for clarity. Like reference characters and/or numerals in the drawings denote like elements, and thus their description may be omitted.

FIG. 1 is a conceptual diagram of a SQUID sensor module according to an example embodiment of the present disclosure.

Referring to FIG. 1, a SQUID sensor module may include a pick-up coil 601 and a SQUID sensor 646. The SQUID sensor 646 may include an input coil 646a and a SQUID 646b. The SQUID sensor 646 may be connected to a circuit unit 602. The pick-up coil 601 may be made of a superconductor material, such as NbTi, covering a bobbin provided in the form of a G-10 epoxy rod. The SQUID sensor 646 may include an input coil disposed on a semiconductor substrate and a Josephson junction electrically connected to the input coil. The input coil 646a and the pick-up coil 601 may be connected with each other through an Nb line using a sonic wedge bonder.

Figure 2A:
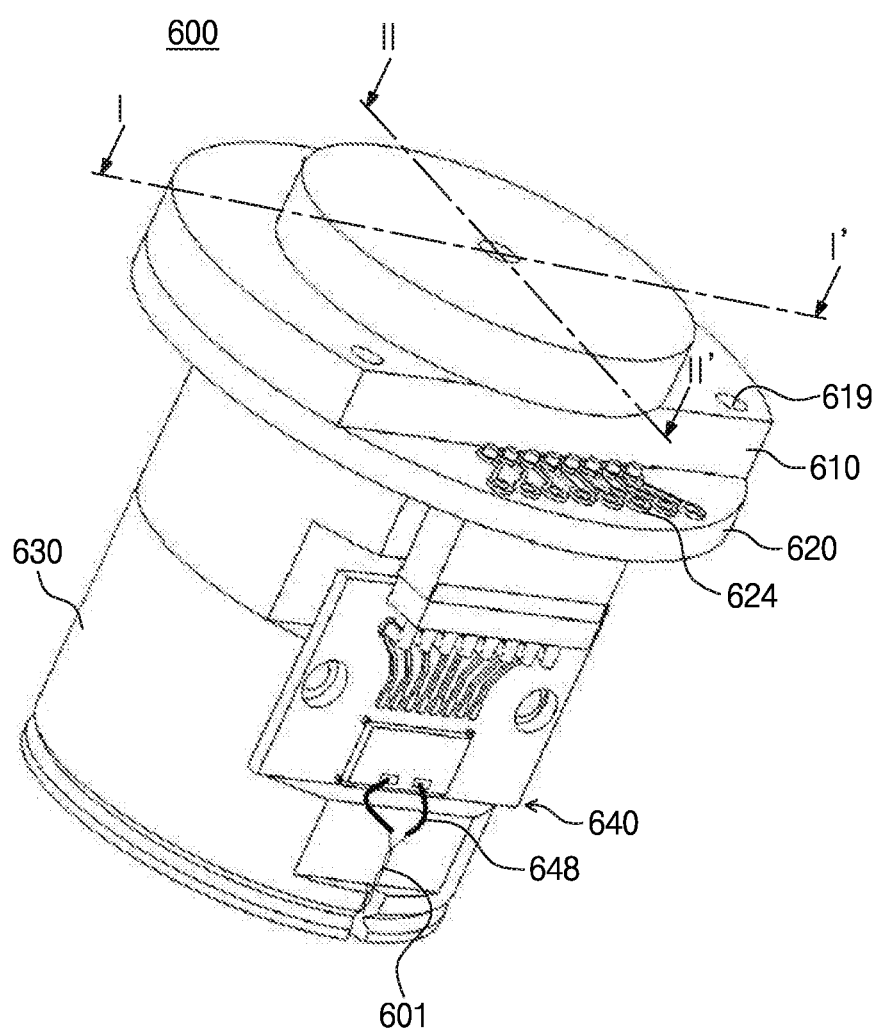
FIG. 2A is a combined perspective view of a SQUID sensor module according to an example embodiment of the present disclosure.

FIG. 2A is a combined perspective view of a SQUID sensor module according to an example embodiment of the present disclosure.

Figure 2B:
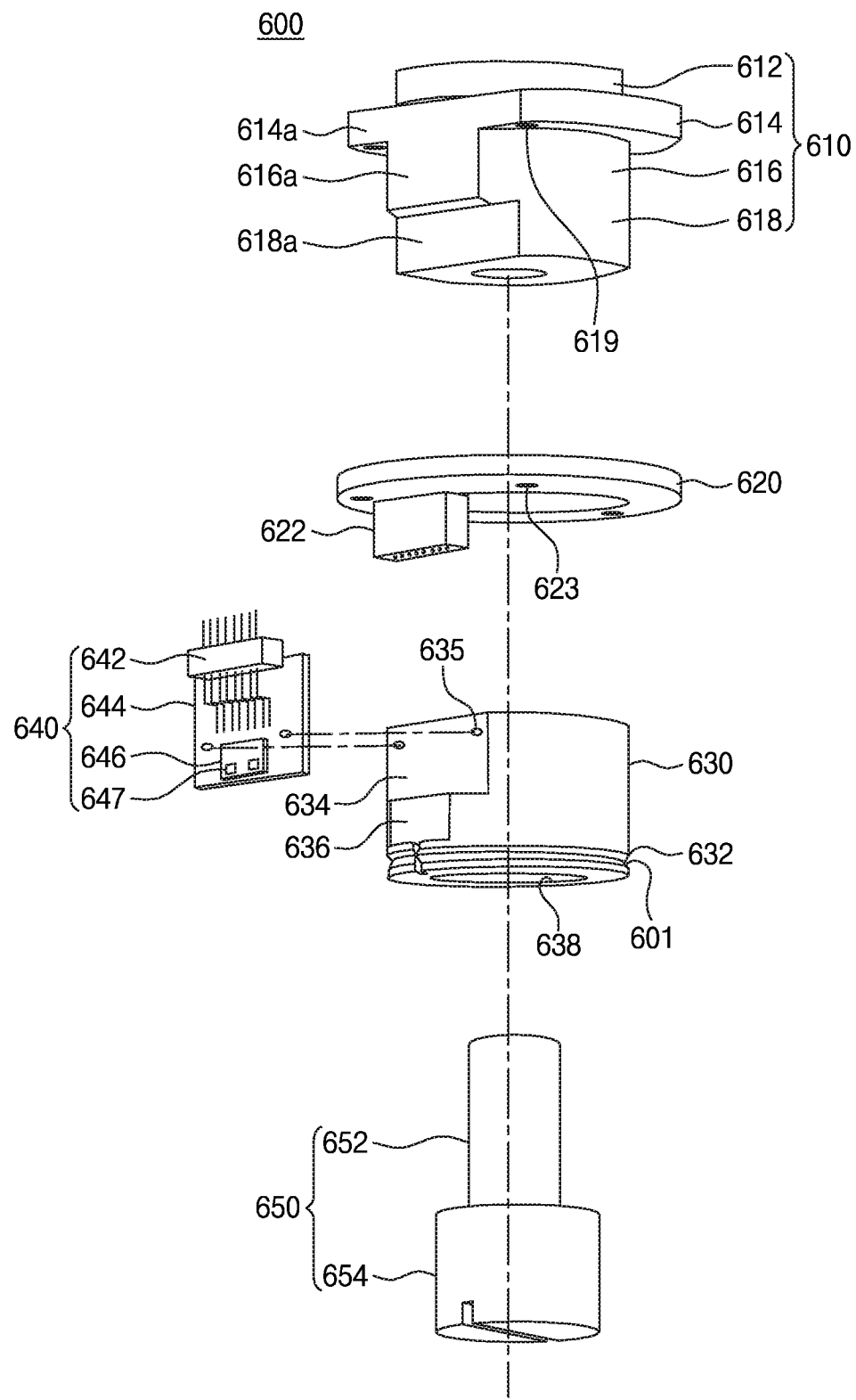
FIG. 2B is an exploded perspective view of the SQUID sensor module in FIG. 2A.

FIG. 2B is an exploded perspective view of the SQUID sensor module in FIG. 2A.

Figure 2C:
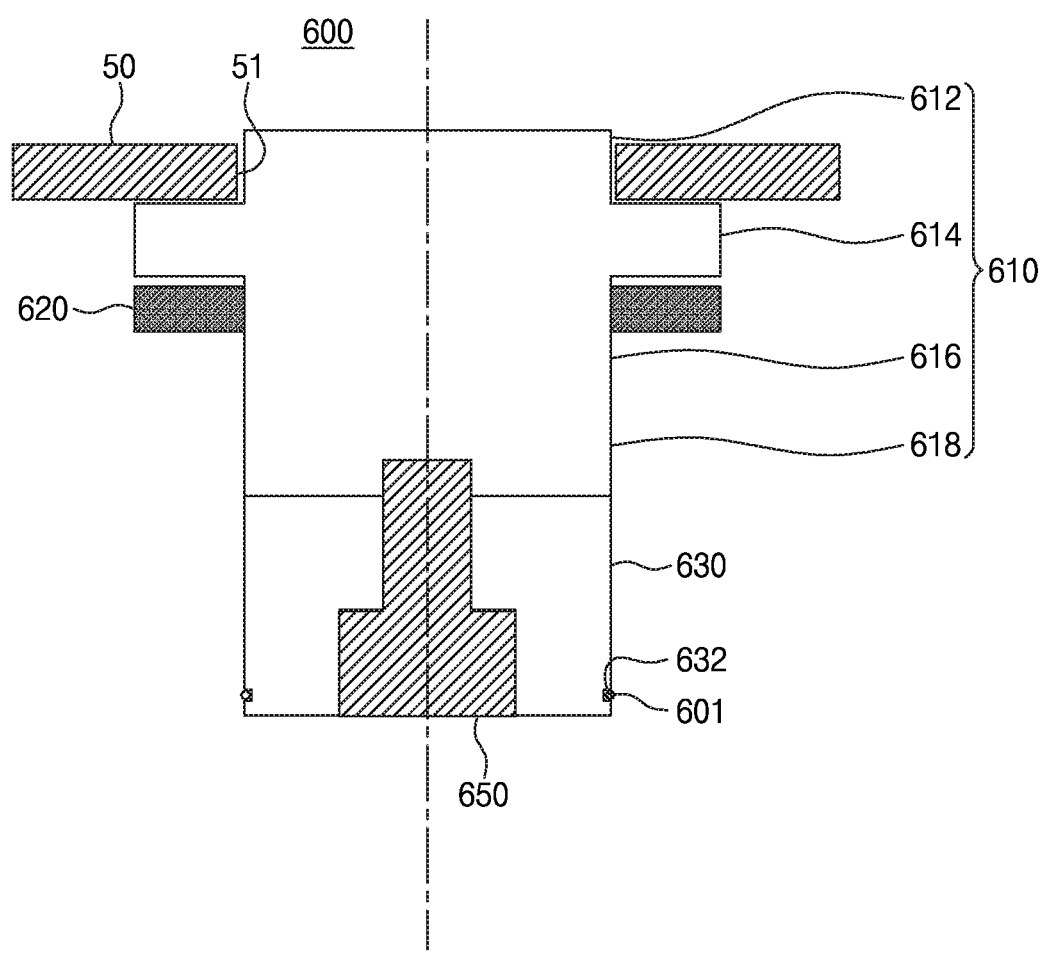
FIG. 2C is a cross-sectional view taken along the line I-I' in FIG. 2A.

FIG. 2C is a cross-sectional view taken along the line I-I' in FIG. 2A.

Figure 2D:
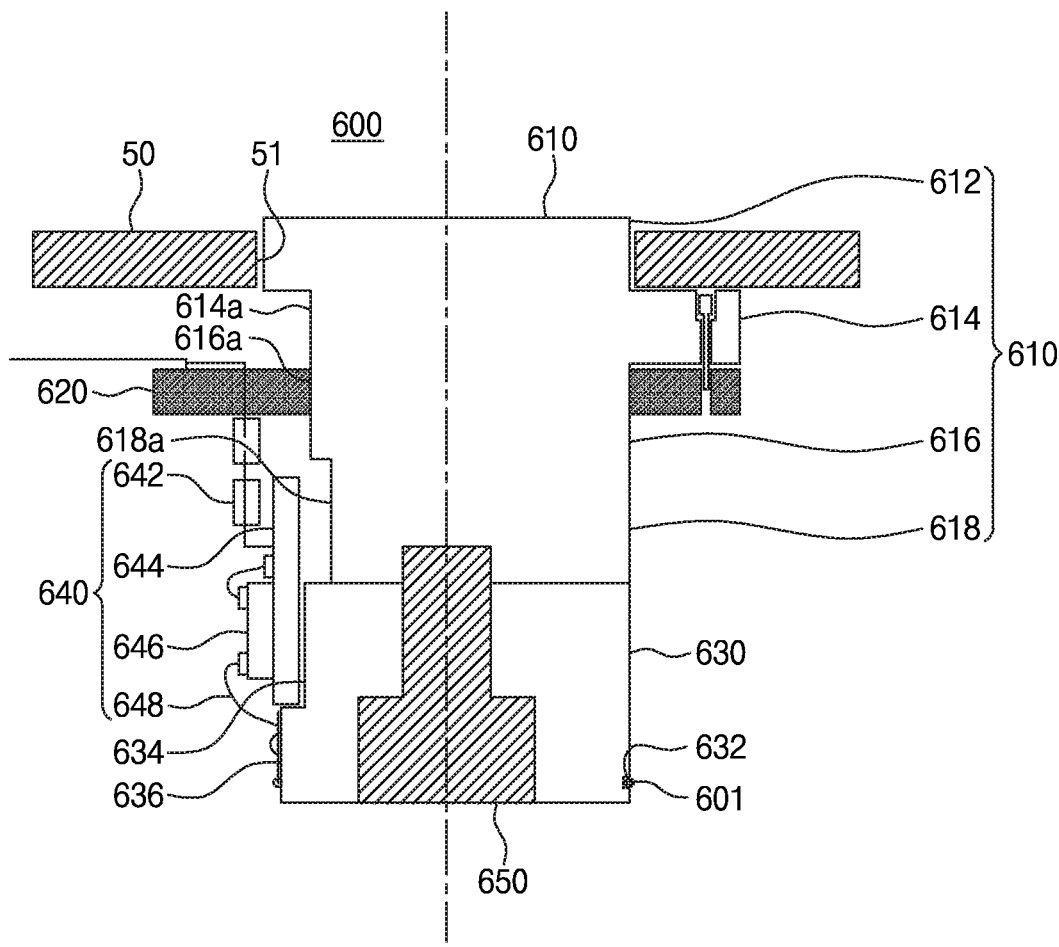
FIG. 2D is a cross-sectional view taken along the line II-II' in FIG. 2A.

FIG. 2D is a cross-sectional view taken along the line II-II' in FIG. 2A.

Referring to FIGS. 2A through 2D, a superconducting quantum interference device (SQUID) sensor module 600 may include a fixed block 610 having one end fixed to a supporting part 50, a bobbin 630 having one end combined with the other end of the fixed block 610 and a groove in which a pick-up coil 601 is wound, a bobbin fixing or attachment structure or material 650 fixed to the other end of the fixed block 610 via a through-hole formed in the center of the bobbin 630, a SQUID printed circuit board (PCB) 640 disposed on an upper side surface of the bobbin 630 and including a SQUID sensor 646, and a signal line connection PCB 620 inserted into an outer circumferential surface of the fixed block 610 and adapted to transmit a signal detected in the SQUID sensor 646 to an external circuit.

The supporting part 50 may be mounted on the SQUID sensor module 600 and be disposed inside a Dewar. The supporting part 50 may be made of a nonmagnetic material. The supporting part 50 may be a sensor-mounted helmet on which the SQUID sensor module 600 is mounted.

The fixed block 610 may be made of a nonmagnetic material such as G10 epoxy in an integral type. The fixed block 610 may be inserted into a through-hole 51 formed at the supporting part 50 to be fixed through an adhesive. The fixed block 610 may include a fixed block protruding portion 612, a fixed block threshold portion 614, a fixed block body portion 616, and a fixed block extending portion 618.

The fixed block protruding portion 612 may have a disc shape and be combined with a groove or the through-hole 51 formed at the supporting part 50. Also the fixed block protruding portion 612 may be fixed to the through-hole 51 through an adhesive.

The fixed block threshold portion 614 may have a disc shape and be continuously connected to the fixed block protruding portion 612. The fixed block threshold portion 614 may have a larger diameter than the fixed block protruding portion 612. The fixed block threshold portion 614 may have a flat side surface 614a. The one side surface 614a of the fixed block threshold portion may be a plane having a constant first vertical distance from a cylindrical central shaft. The fixed block threshold portion 614 may perform a function of alignment in a direction of the central shaft. A through-hole 619 may be formed on an exterior of the fixed block threshold portion 614.

The fixed block body portion 616 may be a portion combined with the signal line connection PCB 620. The signal line connection PCB 620 may be inserted into the outer circumferential surface of the fixed block body portion 616. The signal line connection PCB 620 may have a hole formed on its outer circumference. The through-hole 619 of the fixed block threshold portion 614 may be aligned with a hole 623 of the signal line connection PCB 620. The fixing or attachment structure or material may be inserted into the through-hole 619 of the fixed block threshold portion 614 and the hole 623 of the signal line connection PCB 620 to fix the fixed block threshold portion 614 and the signal line connection PCB 620 to each other. An internal diameter of the signal line connection PCB 620 may be substantially equal to an external diameter of the fixed block body portion 616. An external diameter of the signal line connection PCB 620 may be substantially equal to that of the fixed block threshold portion 614.

The signal line connection PCB 620 may be in the form of a washer having a central through-hole formed therein. When the signal line connection PBC 620 is combined with the outer circumferential surface of the fixed block 610, one side surface of the central through-hole may be a plane to suppress a rotational motion. The signal line connection PCB 620 may include a first connector 622. The first connector 622 may be a female connector. The first connector 622 may be disposed at the edge of a bottom surface of the signal connection PCB 620. A connection terminal 624 and a wiring may be disposed on a top surface of the signal line connection PCB 620. The connection terminal 624 may be connected to the first connector 622 through the wiring. A connection line connected to an external circuit may be combined with the connection terminal 624.

The fixed block body portion 616 may have a disc shape and be continuously connected to the fixed block threshold portion 614. The fixed block body portion 616 may have a smaller diameter than the fixed block threshold portion 614 and have a flat side surface 616a. The side surface 616a of the fixed block body portion 616 may be a plane having a constant second vertical distance from the cylindrical central shaft.

The fixed block extending portion 618 may have the same diameter as the fixed block body portion 616 and have a flat side surface 618a having a diameter equal to that of the fixed block body portion 616. The side surface 618a of the fixed block extending portion 618 may be a plane having a constant third vertical distance from the cylindrical central shaft. The third vertical distance may be smaller than the second vertical distance.

The flat side surface of the fixed block threshold portion 614 may be connected to the flat side surface of the fixed block body portion 616. The side surface 616a of the fixed block body portion 616 and the side surface 618a of the fixed block extending portion 618 may be spaced apart from each other to be parallel to each other. A vertical distance between the central shaft and the side surface 618a of the fixed block extending portion 618 may be smaller than a vertical distance between the central shaft and the side surface 616a of the fixed block body portion 616.

The bobbin 630 may be made of a nonmagnetic material such as G10 epoxy. The bobbin 630 may be in the form of a cylinder. The bobbin 630 may include a first flat portion 634 formed on an upper side surface having a first vertical distance from the central shaft and a second flat portion 636 formed on a lower side surface having a second vertical distance greater than the first vertical distance. The bobbin 630 may have a groove 632 formed at the circumference of a lower side surface. The groove may form a closed loop. The pick-up coil 601 may be wound in the groove 632. A hole 635 may be formed on the first flat portion 634. Fixing or attachment structure or material for fixing a SQUID PCB 640 may be combined with the hole 635. The SQUID PCB 640 may be disposed at the first flat portion 634. Opposite ends of the pick-up coil 601 may be fixed to the second flat portion 636 through an adhesive. The pick-up coil 601 may be electrically connected to the SQUID sensor 646 through a connection line 648 of a superconducting material. The connection line 648 may have an Nb material.

The SQUID PCB 640 may include the SQUID sensor 646 disposed on a PCB substrate 644 and a second connector 642. The SQUID sensor 646 may be in the form of a semiconductor chip. The SQUID sensor 646 may include an input coil and a Josephson junction. The SQUID sensor 646 may include a conductive pad for electrical connection with the pick-up coil 601. The conductive pad 647 may connect the pick-up coil 601. The conductive pad 647 may be electrically connected to another conductive pad. The second connector 642 may be a pin-type male connector. Accordingly, the second connector 642 may be separated from or combined with the first connector 622.

The pick-up coil 601 and the SQUID sensor 646 may be bonded using a connection line of an annealed superconducting material to be directly connected to each other, and an integral-type SQUID magnetometer may be fabricated. The pick-up coil 601 may include a bobbin and a one-turn superconducting wire covering the bobbin. A material of the pick-up coil 601 may be an NbTi wire.

The connection line of an Nb material used in the bonding may be vacuum-annealed at temperature of 1900 degrees centigrade to increase its ductility. Superconducting bonding may be performed using a sonic wedge bonder. Opposite end portions of the pick-up coil 601 may be twisted with each other. Thus, noise of the pick-up coil 601 may be minimized. The pick-up coil 601 may be a first-order gradiometer or a magnetometer.

The bobbin fixing or attachment structure or material 650 may be inserted into a through-hole 638 penetrating the central shaft of the bobbin 630. Thus, the bobbin fixing or attachment structure or material 650 may be fixed to the bottom surface of the fixed block 610. The bobbin fixing or attachment structure or material 650 may be a nonmagnetic material such as G10 epoxy.

When the SQUID PCB 640 is malfunctioned, the bobbin fixing or attachment structure or material 650 may be removed to replace the malfunctioned SQUID PCB 640. In this case, the bobbin 630 and the fixing block 610 may be separated from each other. Thus, the malfunctioned SQUID PCB 640 may be easily replaced with a new SQUID PCB. As a result, maintenance may be readily conducted.

The SQUID sensor module 600 according to an example embodiment of the present disclosure may be inserted into a direct cooling-type Dewar or an indirect cooling-type Dewar to be applied to various apparatuses for measuring a magnetic signal.

Figure 3:
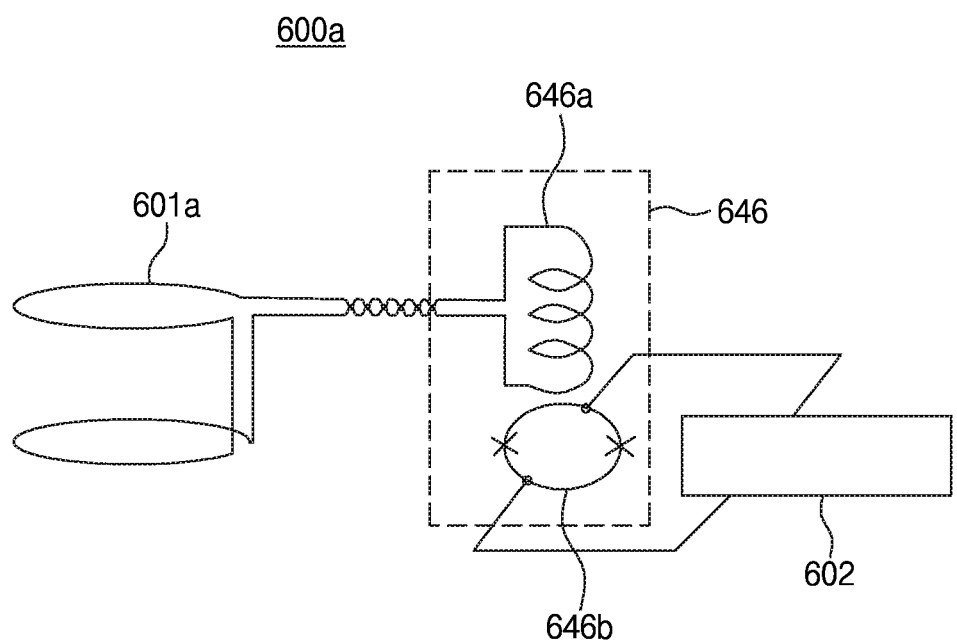
FIG. 3 is a conceptual diagram of a SQUID sensor module according to an example embodiment of the present disclosure.

FIG. 3 is a conceptual diagram of a SQUID sensor module according to an example embodiment of the present disclosure.

Figure 4:
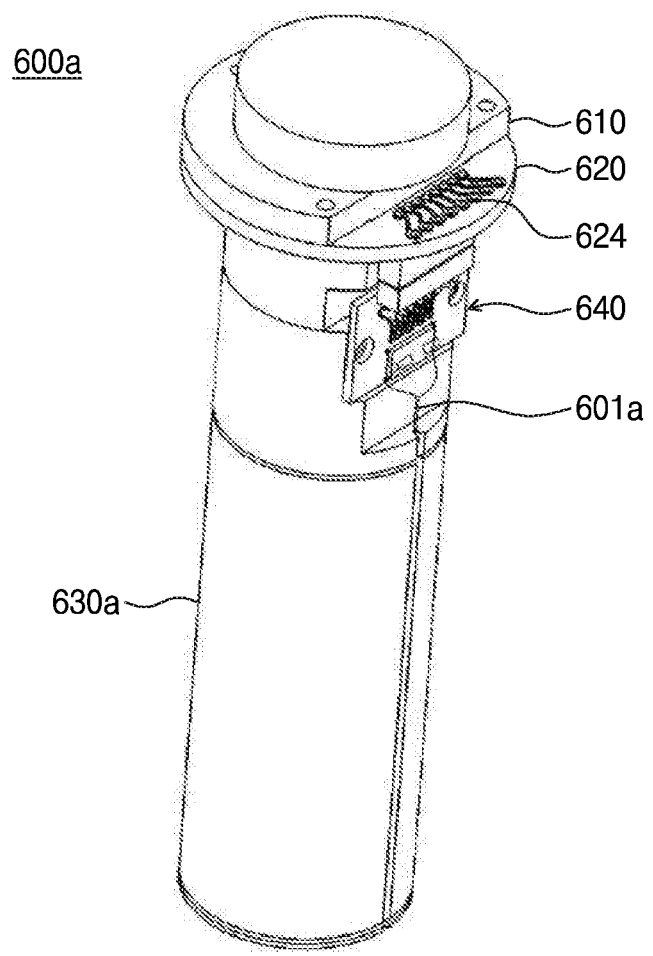
FIG. 4 is a combined perspective view of a SQUID sensor module according to another example embodiment of the present disclosure.

FIG. 4 is a combined perspective view of a SQUID sensor module according to another example embodiment of the present disclosure.

In FIGS. 3 and 4, the same explanations as those made with reference to FIGS. 1 and 2 will be omitted.

Referring to FIGS. 3 and 4, a superconducting quantum interference device (SQUID) sensor module 600a may include a fixed block 610 having one end fixed to a supporting portion, a bobbin 630a having one end combined with the other end of the fixed block 610 and having a groove in which a pick-up coil 601a is wound, a bobbin fixing or attachment structure or material fixed to the other end of the fixed block 610 via a through-hole formed in the center of the bobbin 630a, a SQUID printed circuit board (PCB) 640 disposed on an upper side surface of the bobbin 630 and including a SQUID sensor, and a signal line connection PCB inserted into an outer circumferential surface of the fixed block 610 and adapted to transmit a signal detected in the SQUID sensor to an external circuit.

The supporting part may be mounted on the SQUID sensor module 600a and be disposed inside a Dewar. The supporting part may be made of a nonmagnetic material. The supporting part may be a sensor-mounted helmet on which a sensor is mounted.

The pick-up coil 601a may be a first-order axial gradiometer. Thus, length of the bobbin 630a on which the pick-up coil 601a is wound may increase. The pick-up coil 601 may include a pair of one-turn coils that are continuously connected and wound in opposite directions.

The SQUID sensor module 600a according to an example embodiment of the present disclosure may be inserted into a direct cooling-type Dewar or an indirect cooling-type Dewar to be applied to various apparatuses for measuring a magnetic signal.

Figure 5:
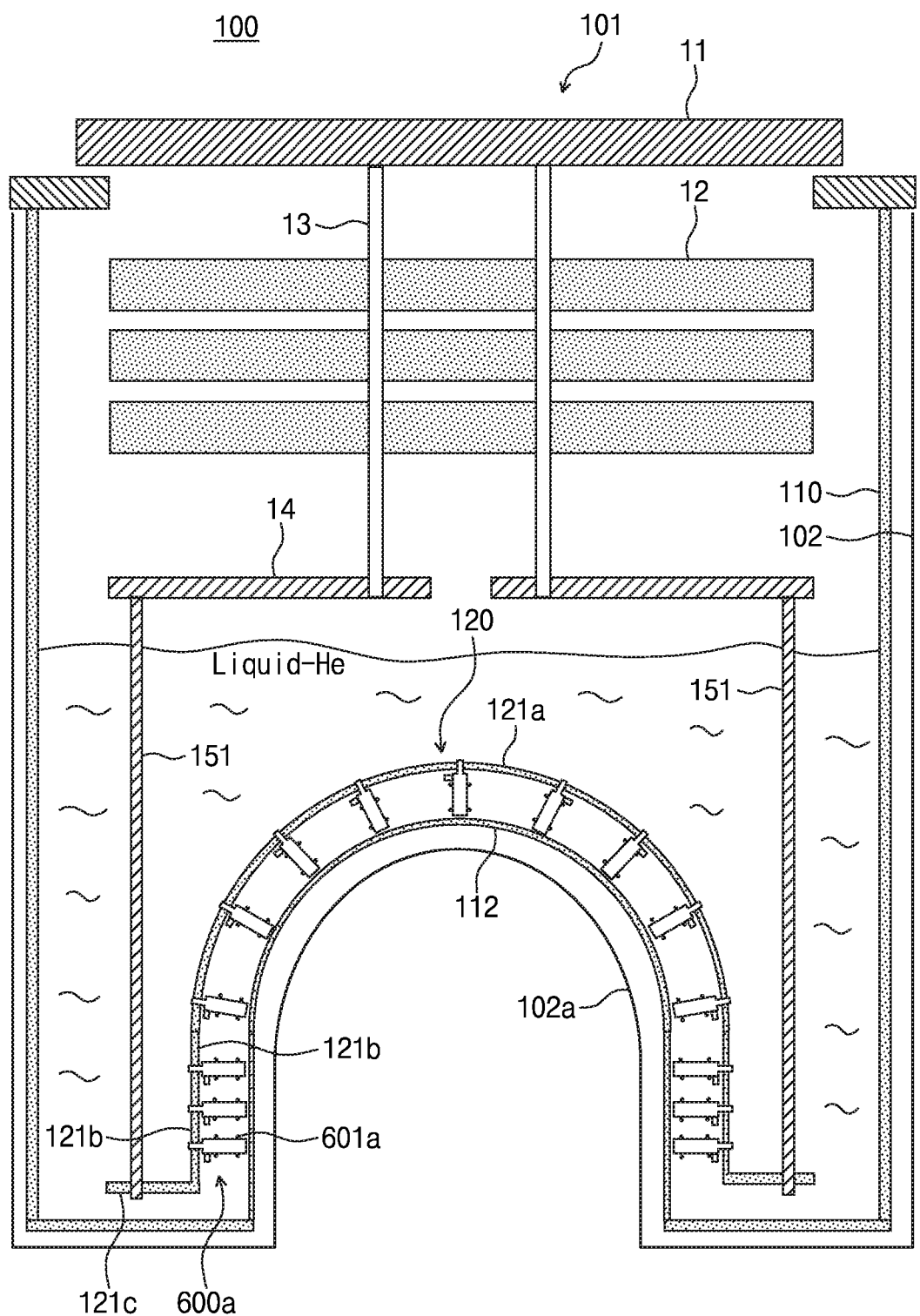
FIG. 5 illustrates a magnetoencephalography (MEG) measuring apparatus according to an example embodiment of the present disclosure.

FIG. 5 illustrates a magnetoencephalography (MEG) measuring apparatus according to an example embodiment of the present disclosure.

Referring to FIG. 5, a magnetoencephalography (MEG) measuring apparatus 100 may include an inner container 110 storing a liquid refrigerant and including an inner helmet 112, an outer container 102 including an outer helmet 102a disposed to cover the inner helmet 112, a sensor-mounted helmet 120 disposed inside the inner container 112, and a superconducting quantum interference device (SQUID) sensor module 600a mounted on the sensor-mounted helmet 120.

The MEG measuring apparatus 100 may include the outer container 102, the inner container 110 disposed inside the outer container 102, and a first insert 101 inserted into the inner container 110.

The inside of the inner container 110 may be filled with a liquid refrigerant. The first insert 101 may include an insert top plate 11, an insert baffle 12 disposed below the insert top plate 11, a guide rod 13 supporting the insert baffle 122 an fixed to the insert top plate 11, a support plate 14 fixed to the guide rod 13, a support rod 151 connected to the support plate 14, and a SQUID sensor module 600a mounted on the sensor-mounted helmet 120.

The first insert 101 may be inserted into the inner container 110 to perform an adiabatic function. The first insert 101 may include the insert top plate 11, the guide rod 13 perpendicularly combined with the insert top plate 11, an insert baffle 12 inserted into the guide rod 13, the support plate 14 for fixing the sensor-mounted helmet 120, and the support rod 151 connecting the support plate 14 and the sensor-mounted helmet 120 to each other.

The insert top plate 11 may be in the form of a disc and be made of G-10 epoxy. The insert top plate 11 may be fixed to a top plate of the outer container 102.

The guide rod 13 may be made of G-10 epoxy and be in the form of a rod or a pipe. The guide rod 13 may be means or structure for supporting the insert baffle 12.

The insert baffle 12 may include Styrofoam with superior warmth retention and a conductive plate. The conductive plate may include an aluminum-coated Mylar layer and a copper layer. The insert baffle 12 may block external thermal conductivity and influx of radiant heat.

The support plate 14 may be made of G-10 epoxy and be in the form of a washer. The support plate 14 may fix the sensor-mounted helmet 120 through the support rod 151.

The support rod 151 may be made of G-10 epoxy and be in the form of a rod. The support rod 151 may be provided in plurality, be connected to the support plate 14, and perpendicularly extend to be connected to the sensor-mounted helmet 120.

The outer container 102 may include the outer helmet 102 disposed on its bottom surface, and the inner container 110 may include the inner helmet 112 disposed on its bottom surface. The outer helmet 102a, the inner helmet 112, and the sensor-mounted helmet 120 may be aligned.

The SQUID sensor module 600a may include a gradiometer as a pick-up coil. The first insert 101 may be an MEG insert including a conventional gradiometer pick-up coil having a base line of 50 mm. The first insert 101 does not use a superconducting shield. The first insert 101 is submerged in the liquid refrigerant of the inner container 110 of a Dewar to be cooled. A wire-wound gradiometer was used as the pick-up coil 601a. The pick-up coil 601a, where a signal coil and a reference coil are wound in opposite direction, includes a pair of coils spaced apart from each other in a fixed distance. A length of a base line between the signal coil and the reference coil is 50 mm. The number of pick-up coils 601a uniformly mounted on a surface of a sensor-mounted helmet 120 was 152. The pick-up coil 601a and the SQUID sensor 646 may be fabricated and integrated into a single module to be directly wound on the liquid refrigerant.

The sensor-mounted helmet 120 may include a hemispherical portion 121a, a cylindrical straight portion 121b continuously connected to the hemispherical portion 121a, and a washer-shaped brim 121c extending from a bottom surface to the outside of the straight portion 121b. The brim 121c may be connected to an insert body through the support rod 151. The insert body may include a plurality of insert baffles to prevent evaporation of the refrigerant. The SQUID sensor module 600a is mounted on the sensor-mounted helmet 120.

Since the first insert 101 is sensitive to external environmental noise, the first insert 101 requires a magnetically shielded room (MSR). Even when the magnetically shielded room is used, many high-priced Permalloys may be used because it is difficult to magnetically shield a low-frequency element.

However, a compact MEG measuring apparatus employing a SQUID sensor module according to an example embodiment of the present disclosure may reduce the consumption amount of a refrigerant such as liquid helium.

Hereinafter, a magnetoencephalography (MEG) measuring apparatus on which a SQUID sensor module according to an example embodiment of the present disclosure is mounted will now be described.

A SQUID sensor module according to an example embodiment of the present disclosure may be combined with a superconducting shielding part to be used. A superconducting shielding material employed a lead (Pb) plate having purity of 99.95 percent and thickness of 0.5 mm.

To confirm the shielding effect at a helmet-type superconducting shielding structure, a magnetic field was applied to a helmet using a coil having a Helmholtz structure and a shielding factor was measured and compared according to a brim structure and a position of the SQUID sensor inside the helmet.

A magnetic shielding factor is defined as below:

$$\text{Shielding Factor } (S) = \frac{H^{(0)}}{H_{axial}} \quad \text{Equation (1)}$$

wherein $H^{(0)}$ represents the intensity of an external magnetic field and, $H_{axial}$ represents the intensity of an axial magnetic field.

When a superconducting shielding helmet is fabricated, a magnetic-force line expelled from the center of a shielding material is focused on the edge to make flux density of the edge higher than when the edge is not shielded. In addition, an incident angle of the magnetic-force line to a pick-up coil spaced to be perpendicular to a superconducting shielding surface increase. Thus, a detected flux (=B A sin θ) increases (B being the intensity of the magnetic field, A being an area of the pick-up coil, and θ being an angle between the magnetic field and a normal line of the pick-up coil). For this reason, magnetic noise of the SQUID sensor disposed at the edge of the helmet further increases due to the superconducting shield.

The shape of the helmet edge was changed to understand an influence of external noise on a SQUID sensor module. First, a virtual test was performed on a helmet having a unidirectional brim. Second, a brim was formed in both directions to optimize a magnetic field distribution and a magnetic-force line direction at a position where a pick-up coil of the SQUID sensor was disposed. In case of a bidirectional brim, length or width of an outwardly formed brim was 50 mm and length or width of an inwardly formed brim was 30 mm. A perpendicularly spaced distance between a superconducting shielding surface and the pick-up coil was designed to be equal to the width of the inwardly formed brim. That is, the length or the width of the inwardly formed brim is made equal to the perpendicularly spaced distance of the pick-up coil to minimize an incident angle of a magnetic-force line that is incident on the pick-up coil.

Figure 6:
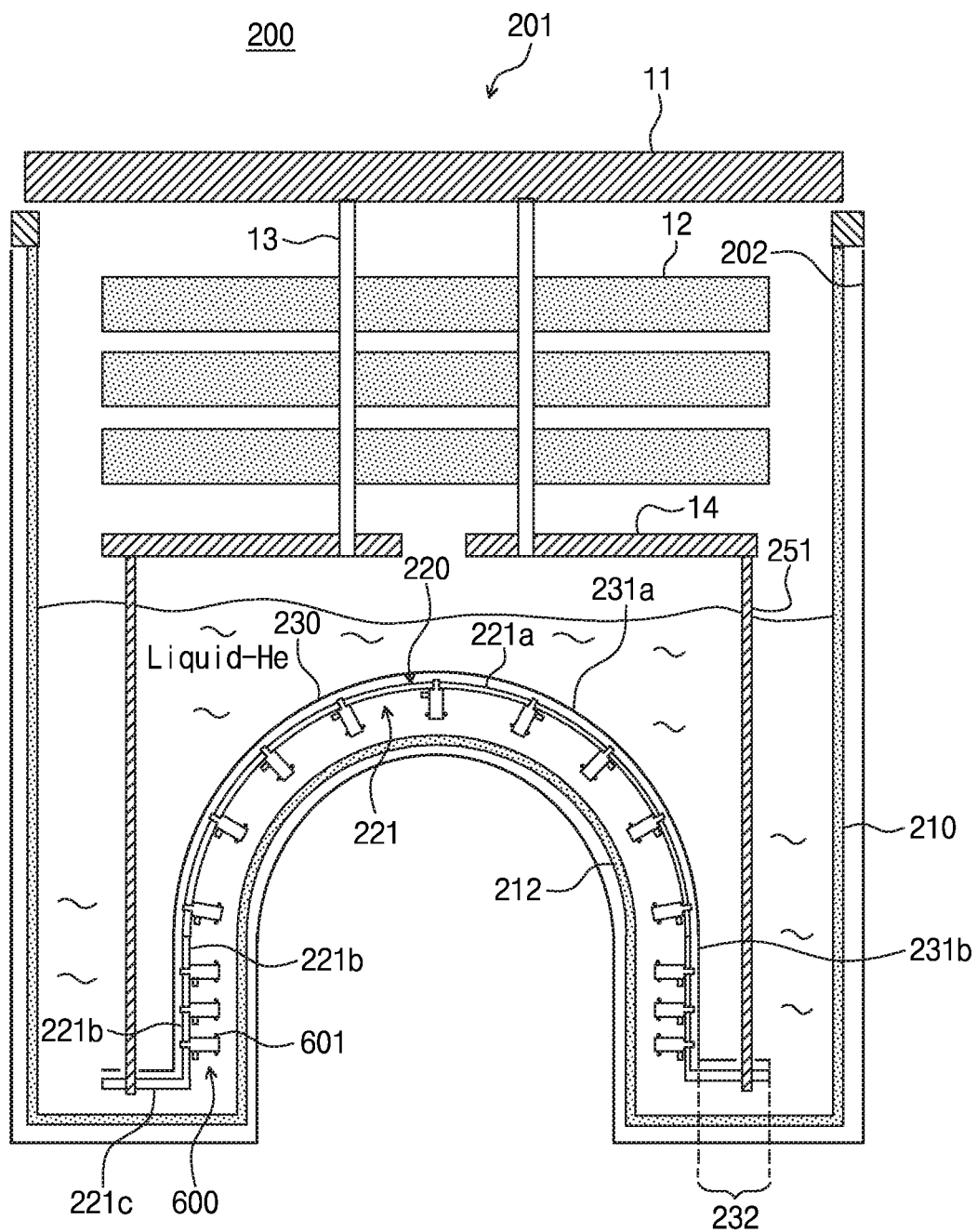
FIG. 6 illustrates a magnetoencephalography (MEG) measuring apparatus according to another example embodiment of the present disclosure.

FIG. 6 illustrates a magnetoencephalography (MEG) measuring apparatus according to another example embodiment of the present disclosure.

Referring to FIG. 6, a magnetoencephalography (MEG) measuring apparatus 200 includes an inner container 210 storing a liquid refrigerant and including an inner helmet, an outer container 202 including an outer helmet disposed to cover the inner helmet 212, a sensor-mounted helmet 220 disposed inside the inner container 212, and a superconducting quantum interference device (SQUID) sensor module 600 mounted on the sensor-mounted helmet 220.

The MEG measuring apparatus 200 may include the outer container 202, the inner container 210 disposed inside the outer container 202, and a second insert 201 inserted into the inner container 210.

The second insert 201 may be inserted into the inner container 210 to perform an adiabatic function. The second insert 201 may include an insert top plate 11, a guide rod 13 combined with the insert top plate 11 and extending perpendicularly, an insert baffle 12 inserted into the guide rod 13, a support plate 14 for fixing the sensor-mounted helmet 220, and a support rod 251 connecting the support plate 14 and the sensor-mounted helmet 220 to each other.

The insert top plate 11 may be in the form of a disc and be made of G-10 epoxy. The insert top plate 11 may be fixed on a top plate of the outer container 202.

The guide rod 13 may be made of G-10 epoxy and be in the form of a rod or a pipe. The guide rod 13 may be means or structure for supporting the insert baffle 12.

The insert baffle 12 may include Styrofoam with superior warmth retention and a conductive plate. The conductive plate may include an aluminum-coated Mylar layer and a copper layer. The insert baffle 12 may block external thermal conductivity and influx of radiant heat.

The support plate 14 may be made of G-10 epoxy and be in the form of a washer. The support plate 14 may fix the sensor-mounted helmet 220 through the support rod 251.

The support rod 251 may be made of G-10 epoxy and be in the form of a rod. The support rod 251 may be provided in plurality, be connected to the support plate 14, and perpendicularly extend to be connected to the sensor-mounted helmet 220.

The outer container 202 may include the outer helmet 202a disposed on its bottom surface, and the inner container 210 may include the inner helmet 212 disposed on its bottom surface. The outer helmet 202a, the inner helmet 212, and the sensor-mounted helmet 220 may be aligned. The SQUID sensor module 600 is mounted on the sensor-mounted helmet 220.

The second insert 201 may include a superconducting shielding helmet 230 having an outward brim structure. The superconducting shielding helmet 230 of the outward brim structure was fabricated using a lead plate having purity of 99.95 percent. A sensor-mounted helmet 220 is mounted inside the superconducting shielding helmet 230. The second inset 201 may be a superconducting shielding helmet-type MEG insert having an outward brim.

The SQUID sensor module 601 may include a gradiometer as a pick-up coil. The second insert 201 uses a superconducting shield. The second insert 201 is submerged in a liquid refrigerant in the inner container 201 of a Dewar to be cooled. A one-turn magnetometer was used as the pick-up coil 601. The number of pick-up coils 601 uniformly mounted on a surface of the sensor-mounted helmet 220 was 152. The pick-up coil 601a and the SQUID sensor 646 may be fabricated and integrated into a single module to be directly wound on the liquid refrigerant.

The sensor-mounted helmet 220 may include a hemispherical portion 221a, a cylindrical straight portion 221b continuously connected to the hemispherical portion 221a, and a washer-shaped brim 221c extending from a bottom surface to the outside of the straight portion 221b. The brim 221c may be connected to an insert body through the support rod 251. The insert body may include a plurality of insert baffles to prevent evaporation of the refrigerant.

The pick-up coil 601 includes a bobbin and a one-turn NbTi wire covering the bobbin. The pick-up coil 601 and a SQUID sensor 646 may be fabricated and integrated into a single module to be disposed at the sensor-mounted helmet 220. The sensor-mounted helmet 220 is connected to an insert body through a support rod 251. The superconducting shielding helmet 230 and the sensor-mounted helmet 220 are submerged in a liquid refrigerant to be cooled.

In case of a superconducting shielding helmet-type MEG manufacturing apparatus having an outward brim, fifteen reference SQUID sensor channels (not shown) at five points in a three-dimensional vector manner to use an adaptive filter. The reference SQUID sensor channel (not shown) is disposed outside the superconducting shielding helmet 230.

The superconducting shielding helmet 230 includes a hemispherical portion 231a, a cylindrical straight portion 231b continuously connected to the hemispherical portion 231a, and a washer-shaped outward brim 232 extending from a bottom surface to the outside of the straight portion 231b.

The superconducting shielding helmet-type MEG measuring apparatus 200 having an outward brim may reduce weight of a magnetically shielded room. However, the superconducting shielding helmet-type MEG measuring apparatus 200 having an outward brim requires a reference SQUID sensor channel. In addition, the superconducting shielding helmet-type MEG measuring apparatus 200 having an outward brim may not measure well an MEG signal generated at an auditory cortex or a visual cortex in the vicinity of the edge of the superconducting helmet. Thus, a superconducting helmet having another structure is required to measure the MEG signal generated at the auditory cortex or the visual cortex.

Hereinafter a superconducting helmet having another structure to measure an MEG signal generated at an auditory cortex and a visual cortex will now be described.

Figure 7A:
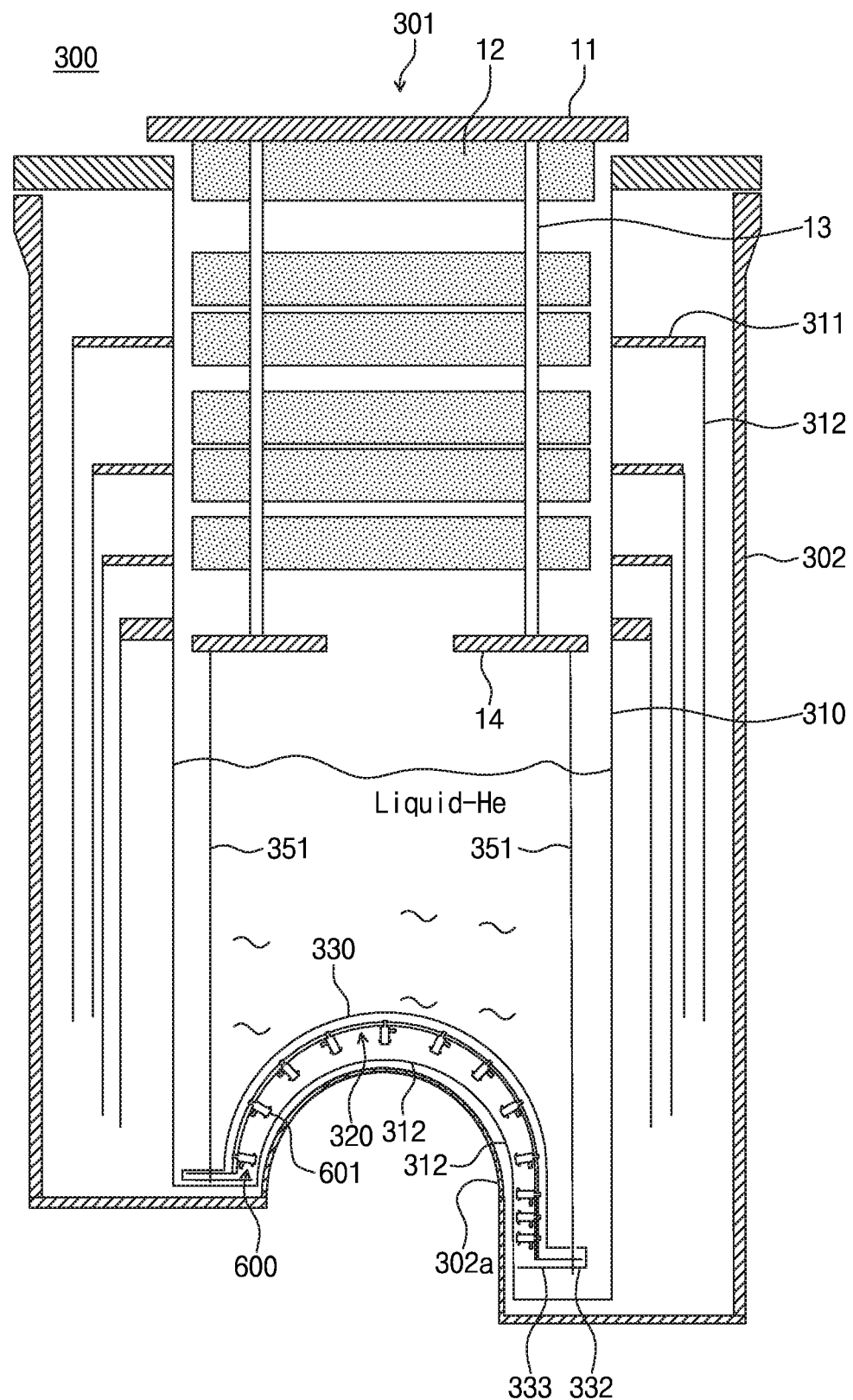
FIG. 7A illustrates a magnetoencephalography (MEG) measuring apparatus according to another example embodiment of the present disclosure.

FIG. 7A illustrates a magnetoencephalography (MEG) measuring apparatus according to another example embodiment of the present disclosure.

Figure 7B:
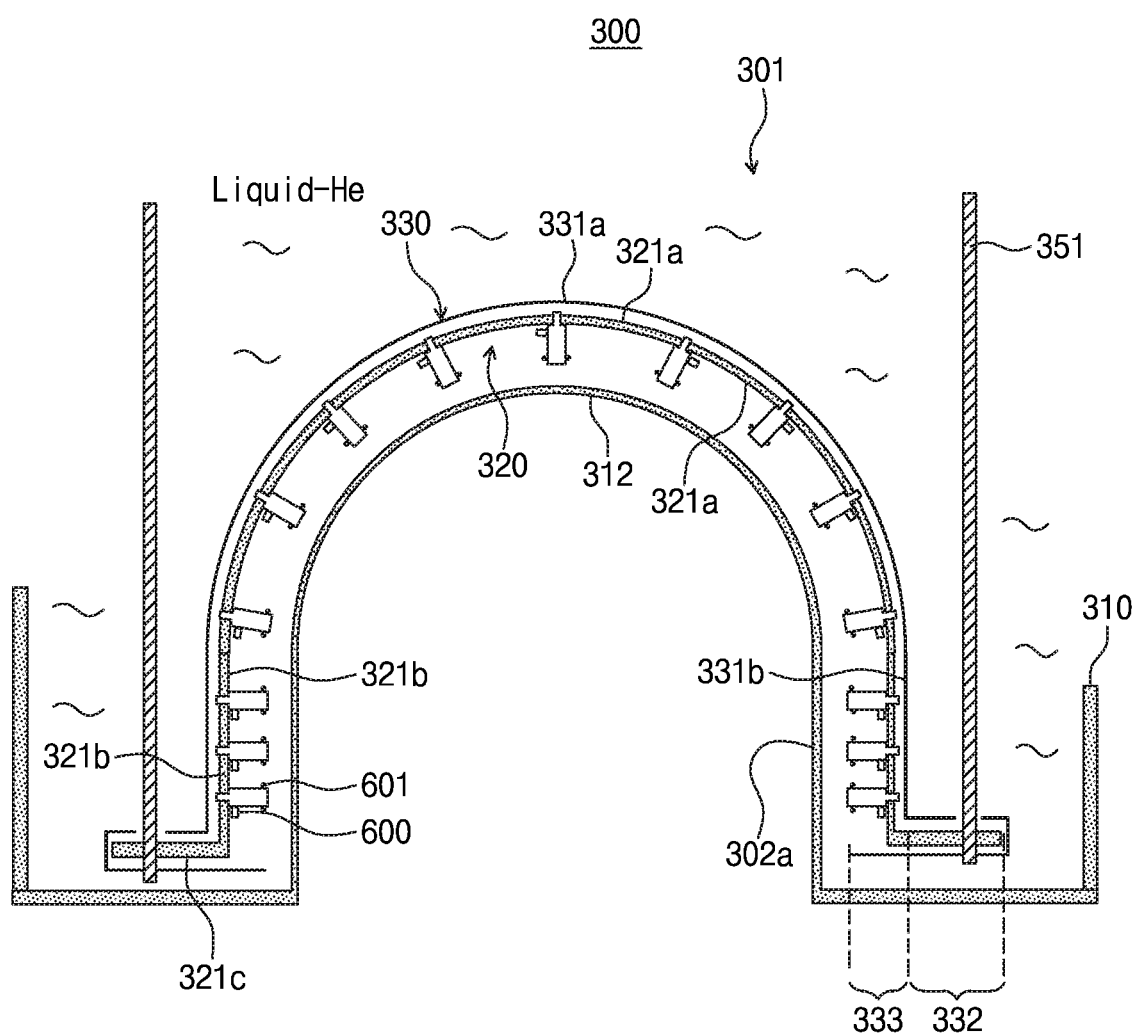
FIG. 7B illustrates a superconducting shielding helmet-type insert of a bidirectional brim structure.

FIG. 7B illustrates a superconducting shielding helmet-type insert of a bidirectional brim structure.

Figure 7C:
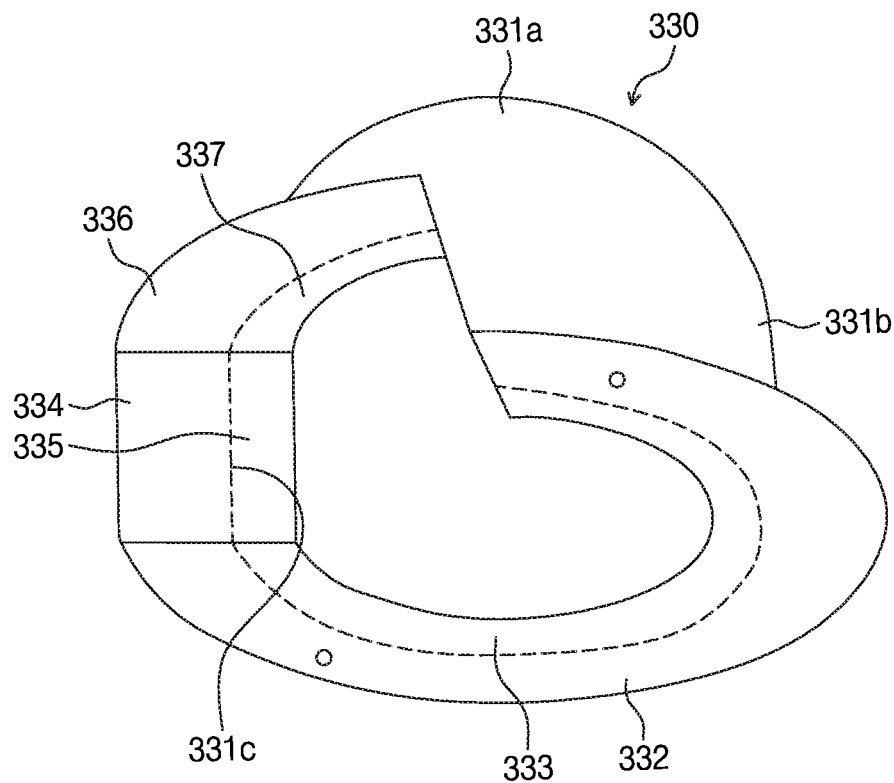
FIG. 7C is an exploded perspective view of a superconducting shielding helmet and a sensor-mounted helmet.
Figure 7C:
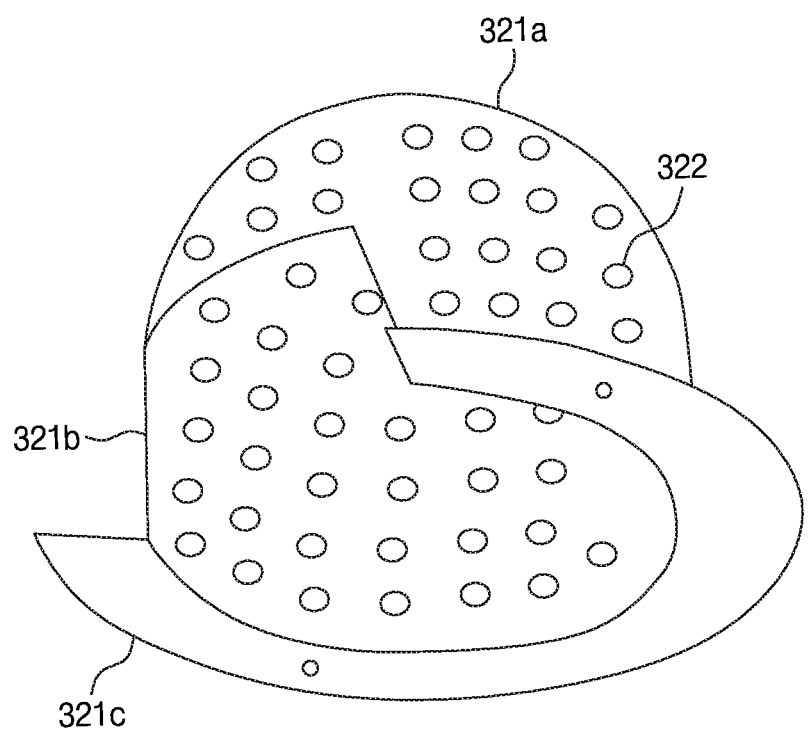

FIG. 7C is an exploded perspective view of a superconducting shielding helmet and a sensor-mounted helmet.

Referring to FIGS. 7A through 7C, a magnetoencephalography (MEG) measuring apparatus 300 may include an inner container 310 storing a liquid refrigerant and including an inner helmet 312, an outer container 302 including an outer helmet 302a disposed to cover the inner helmet 312, a sensor-mounted helmet 320 disposed inside the inner container 312, and a superconducting quantum interference device (SQUID) sensor module 600 mounted on the sensor-mounted helmet 320.

The MEG measuring apparatus 300 may include the outer container 302, the inner container 310 disposed inside the outer container 302, and a third insert 301 inserted into the inner container 310. The inside of the inner container 310 may be filled with a liquid refrigerant.

The third insert 301 may be inserted into the inner container 310 to perform an adiabatic function. The third insert 301 may include an insert top plate 11, a guide rod 13 combined with the insert top plate 11 and extending perpendicularly, an insert baffle 12 inserted into the guide rod 13, a support plate 14 for fixing the sensor-mounted helmet 320, and a support rod 351 connecting the support plate 14 and the sensor-mounted helmet 320 to each other. The SQUID sensor module 600 may be mounted on the sensor-mounted helmet 320.

The third insert 301 may include a superconducting shielding helmet 330 having a bidirectional brim structure. A lead plate having purity of 99.95 percent was fabricated in the form of a helmet to use a superconducting shield in a helmet-type MEG. A sensor-mounted helmet 320 is mounted inside the superconducting shielding helmet 330. A magnetometer was used as the pick-up coil 601. The number of pick-up coils 601 uniformly mounted on a surface of the sensor-mounted helmet 320 was 152. The pick-up coil 601 and a SQUID sensor 646 may be fabricated and integrated into a single module to be mounted on the sensor-mounted helmet 320. The magnetometer may include a bobbin and a one-turn NbTi wire covering the bobbin.

Connection between the SQUID sensor 342 and the pick-up coil 341 was achieved not using an aid such an Nb plate and an Nb screw but using direct bonding for integration of an MEG apparatus. This integration results in the advantage that stray inductance between the pick-up coil 341 and the SQUID sensor 342 may decrease to about one-tenth to significantly improve a balance factor. An Nb wire used in the bonding was vacuum-annealed at temperature of 1900 degrees centigrade to increase ductility of the Nb wire. The superconducting shield employs a sonic wedge bonder. A SQUID PCB with the mounted the SQUID sensor 646 was fixed to a fixing block attached to the sensor-mounted helmet 320 by using a plastic screw.

The MEG measuring apparatus 300 includes a superconducting helmet 330 including an inward brim 333, the sensor-mounted helmet 320 disposed inside the superconducting helmet 330, the pick-up coil 601 disposed inside the sensor-mounted helmet 320, and the SQUID sensor module 600 mounted on the sensor-mounted helmet 320. The SQUID sensor module 600 includes a SQUID sensor connected to the pick-up coil 601.

A Dewar may include an inner container 310 and an outer container 302. The Dewar may have a coaxial cylindrical structure. A space between the outer container 302 and the inner container 310 may be maintained at a vacuum state. The outer container 302 may include a top plate. A through-hole may be formed in the center of the top plate. The inner container 310 may be connected to the through-hole. The outer container 302 may have a cylindrical shape. An external helmet 302a may be disposed on a bottom surface of the outer container 302 to allow a person's head to be inserted.

The inner container 310 may be in the form of a lidless cylinder. An inner helmet 312 aligned with the outer helmet 302 may be disposed on a bottom surface of the inner container 310. A washer-shaped support 311 may be disposed on an outer surface of the inner container 310. A thermal shielding part 312 may be disposed on an outer circumferential surface of the inner container 310. The thermal shielding part 312 may include an upper cylindrical portion and a lower slit portion continuously connected to the upper cylindrical portion. The lower slit portion may have a slit that is perpendicularly formed. The thermal shielding part 312 may be made of a conductive material. A liquid refrigerant may be stored in the inner container 310.

An insert 301 may include an insert body 301a and a measurement portion 301b connected to the insert body 301a. The insert 301 may be inserted into the inner container 310 to perform an adiabatic function. The insert body 301a may include an insert top plate 11, a guide rod 13 combined with the insert top plate 11 and extending vertically, an insert baffle 12 inserted into the guide rod 13, a support plate 14 for fixing the sensor-mounted helmet 320, and a support rod 351 connecting the support plate 14 and the sensor-mounted helmet 320 with each other.

The insert top plate 11 may be in the form of a disc and be made of G-10 epoxy. The insert top plate 11 may be fixed to a top plate of the outer container 302.

The guide rod 13 may be made of G-10 epoxy and be in the form of a rod or a pipe. The guide rod 13 may be means or structure for supporting the insert baffle 12.

The insert baffle 12 may include a Styrofoam with superior warmth retention and a conductive plate. The conductive plate may include an aluminum-coated Mylar layer and a copper layer. The insert baffle 12 may block external thermal conductivity and influx of radiant heat.

The support plate 14 may be made of G-10 epoxy and be in the form of a washer. The support plate 14 may fix the sensor-mounted helmet 320 through the support rod 351.

The support rod 351 may be made of G-10 epoxy and be in the form of a rod. The support rod 351 may be provided in plurality, be connected to the support plate 14, and extend perpendicularly to be connected to the sensor-mounted helmet 320.

The sensor-mounted helmet 320 includes a hemispherical portion 321a, a cylindrical straight portion 321b continuously connected to the hemispherical portion 321a, and an outward brim connected to a bottom surface of the straight portion in an outward direction. The straight portion 321b may be partially removed in a direction that a person's eye views. A plurality of through-holes 322 may be formed at the straight portion 321b and the hemispherical portion 321a of the sensor-mounted helmet 320. A SQUID sensor module is mounted in the through-hole 322.

The sensor-mounted helmet 320 may be made of G-10 epoxy and be fabricated with a plurality of components using an epoxy adhesive. The hemispherical portion 321a may have a hemispherical shape. The shape of the hemispherical portion 321a may be variously modified into, for example, a parabolic shape or an elliptical shape allowing a person's head to be inserted. The straight portion 321b may be continuously connected to the hemispherical portion 321a. Accordingly, the straight portion 321b may have a cylindrical shape. The shape of the straight portion 321b is not limited to the cylindrical shape, and the straight portion 321b may have a greater radius of curvature than the hemispherical portion 321a. The straight portion 321b may be partially removed to provide a visual field ensuring portion. Specifically, an azimuthal element having the range between 45 and 180 degrees may be removed. Thus, a person's eye may ensure a visual field when the person's head is inside the sensor-mounted helmet 320. The outward brim 321c may be in the form of a washer.

The superconducting helmet 330 includes an inward brim 333, an outward brim 332, a hemispherical portion 331, a cylindrical straight portion 331b continuously connected to the hemispherical portion 331a, and a visual field ensuring portion 331c where the straight portion 331b is partially removed. The superconducting helmet 330 may further include an inward side brim 335 disposed at opposite sides of the visual field ensuring portion 331c and connected to the inward brim 333, an outward side brim 334 disposed at opposite sides of the visual field ensuring portion 331c and connected to the outward brim 332, an inward upper brim 337 disposed on the visual field ensuring portion 331c and connected to the inward side brim 335, and an outward upper brim 336 disposed on the visual field ensuring portion 331c and connected to the outward side brim 334. The superconducting helmet 330 may shield external magnetic noise to measure an MEG signal when performance of a magnetically shielded from is degraded or the magnetically shielded room does not exist.

The inward brim 333, the inward side brim 335, and the inward upper brim 337 may be continuously connected. The outward brim 332, the outward side brim 334, and the outward upper brim 336 may be continuously connected. Length or width of the inward brim may be about 20 mm to about 40 mm. A material of the superconducting helmet 330 may be lead (Pb). The superconducting helmet 330 may be fabricated by folding a plate or using a mold. The outward brim 332 of the superconducting helmet 330 may be disposed to cover the outward brim 321c of the sensor-mounted helmet 320.

To compare signal characteristics and external environmental noise characteristics, three types of measurement inserts were evaluated in a magnetically shielded room using the same circuit and the same Dewar. Characteristics of the used magnetically shielded room employed aluminum having high electrical conductivity and a magnetic material having high initial permeability. A magnetic shielding factor of the fabricated magnetically shielded room was 140 times (@0.1 Hz) and 80,000 times (@100 Hz). To measure a magnetic field signal, a SQUID circuit may include a flux-locked-loop (FLL) circuit using a normal front-end amplifier and an analog signal processing circuit ASP for noise filter and amplification of a measured signal. The analog signal processing circuit may include a low-pass filter (100 Hz), a high-pass filter (0.1 Hz), a 60 Hz notch filter, and a 40 dB amplifier.

A helmet with an outward brim having width of 50 mm attached to only the outside of the helmet and a helmet with brims having widths of 50 mm and 30 mm attached to both sides (i.e., an outward brim and an inward brim) are certainly different in magnetic field distribution and magnetic-force line direction. When only the outward brim is formed, a magnetic field is focused toward the inner edge of the helmet and a magnetic field element perpendicular to, i.e., impinging on a surface of a pick-up coil was large.

When not only an outward brim but also an inward brim was inwardly formed by a distance (30 mm) at which the pick-up coil is spaced apart from a superconducting surface, it was confirmed that an angle formed by a magnetic field direction and the surface of the pick-up coil was made smaller. Preferably, length of the inward brim is 30 mm. Also preferably, length of the outward brim is 50 mm. When the length of the inward brim is equal to a spaced distance between the pick-up coil and the superconducting helmet, a magnetic field impinging on the pick-up coil may nearly horizontally imping on the surface of the pick-up coil. Thus, external magnetic noise may be reduced.

Since the intensity of a magnetic signal from a magnetic field signal source decreases in inverse proportion to the square of a distance, a distance between the signal source and a pick-up coil needs to be minimized to improve an SNR. A study was conducted on this method to develop and use a coil-in-vacuum (CIV) SQUID where a pick-up coil is disposed in a vacuum vessel.

In a CIV-type SQUID apparatus, a pick-up coil and a SQUID sensor are disposed to be maintained in a vacuum state. Thus, only a low-temperature refrigerant exists in a helium inner storage container for storing a liquid refrigerant. Thus, there is only a path to fill the refrigerant. Thus, a diameter of a neck portion of the helium inner storage container may be significantly reduced. As a result, an evaporation rate of the liquid refrigerant may be reduced.

In a conventional CIV-type SQUID apparatus, a SQUID sensor and a pick-up coil are connected while being spaced apart from each other to prevent distortion of a magnetic signal. According to this method, manufacturing of the SQUID sensor has a high level of difficulty and maintenance is made difficult after the manufacturing of the SQUID sensor. Moreover, there is the disadvantage that a thermal transfer medium for cooling the pick-up coil must be additionally mounted. A SQUID sensor and a pick-up coil used in the conventional CIV-type SQUID apparatus are combined using a superconducting bolt and a superconducting nut. When the bulky superconducting bolt and nut approach the pick-up coil, a magnetometer measures a distorted magnetic signal. The magnetometer is not capable of accurately measure a signal desired to be measured because a balance factor is significantly reduced. In addition, a low SNR and great signal distortion may cause an important signal source localization error.

In view of the above, the conventional CIV-type SQUID apparatus uses a method for physically separating and fixing the SQUID sensor and the pick-up coil. A fixed position of the SQUID sensor is a position where the low-temperature refrigerant is attached to a bottom or sidewall, and the pick-up coil is fixed to a position adjacent to the signal source. This method suffers from the disadvantage that difficulty in manufacturing of the SQUID sensor and difficulty in combination of a low-temperature refrigerant storage container and the SQUID sensor increase significantly and thus much time and cost are required.

When a conventional CIV SQUID system is used in an MEG apparatus, other problems occur, as follows. A pick-up coil for measuring a biomagnetic signal using a SQUID sensor may be in the form of a magnetometer or a gradiometer.

The magnetometer measures an absolute value of a magnetic field to simultaneously measure a signal source and a neighboring great environmental noise. Thus, SQUID operating characteristics and a signal-to-noise ratio (SNR) greatly vary depending on the neighboring environmental noise. Particularly, in case of an MEG having a very weak signal, a special magnetically shielded room having a very high shielding factor is required.

The gradiometer includes a reference coil and a signal coil. The reference coil and the signal coil are wound in different directions. Thus, the gradiometer measures a differential value of a magnetic signal. Thus, uniform external environmental noise may be almost removed and a magnetic signal generated by a signal source adjacent to the signal coil may be relatively less offset to increase an SNR. If the gradiometer is used, a signal having a high SNR may be obtained in a magnetically shielded room having a lower shielding factor than the magnetometer. However, since length of the gradiometer is much greater than that of the magnetometer, an area occupied by a helmet-type gradiometer apparatus increase. Thus, an area in which radiant heat is received from room temperature also increases, which causes an evaporation rate of a low-temperature refrigerant to significantly increase. Accordingly, there is a need for a CIV MEG apparatus in which a distance between a pick-up coil and a signal source is short while using a magnetometer.

Assuming that a CIV SQUID system is applied to an MEG apparatus using a superconducting shield, a conventional helmet-type superconducting shield is introduced at a helmet edge in a direction of a magnetic force line perpendicular to a detection coil. The helmet-type superconducting shield significantly increases a noise level of a SQUID sensor disposed to be farthest from a vertex. Measurement of an MEG signal generated at an auditory cortex and a visual cortex is greatly limited. Thus, when the superconducting shield is used, a magnetometer may operate similarly to a gradiometer. Nonetheless, if the superconducting shield is used, it is difficult to measure the MEG signal generated at the auditory cortex and the visual cortex. Accordingly, there is a need for superconducting shield having a novel structure.

Figure 8A:
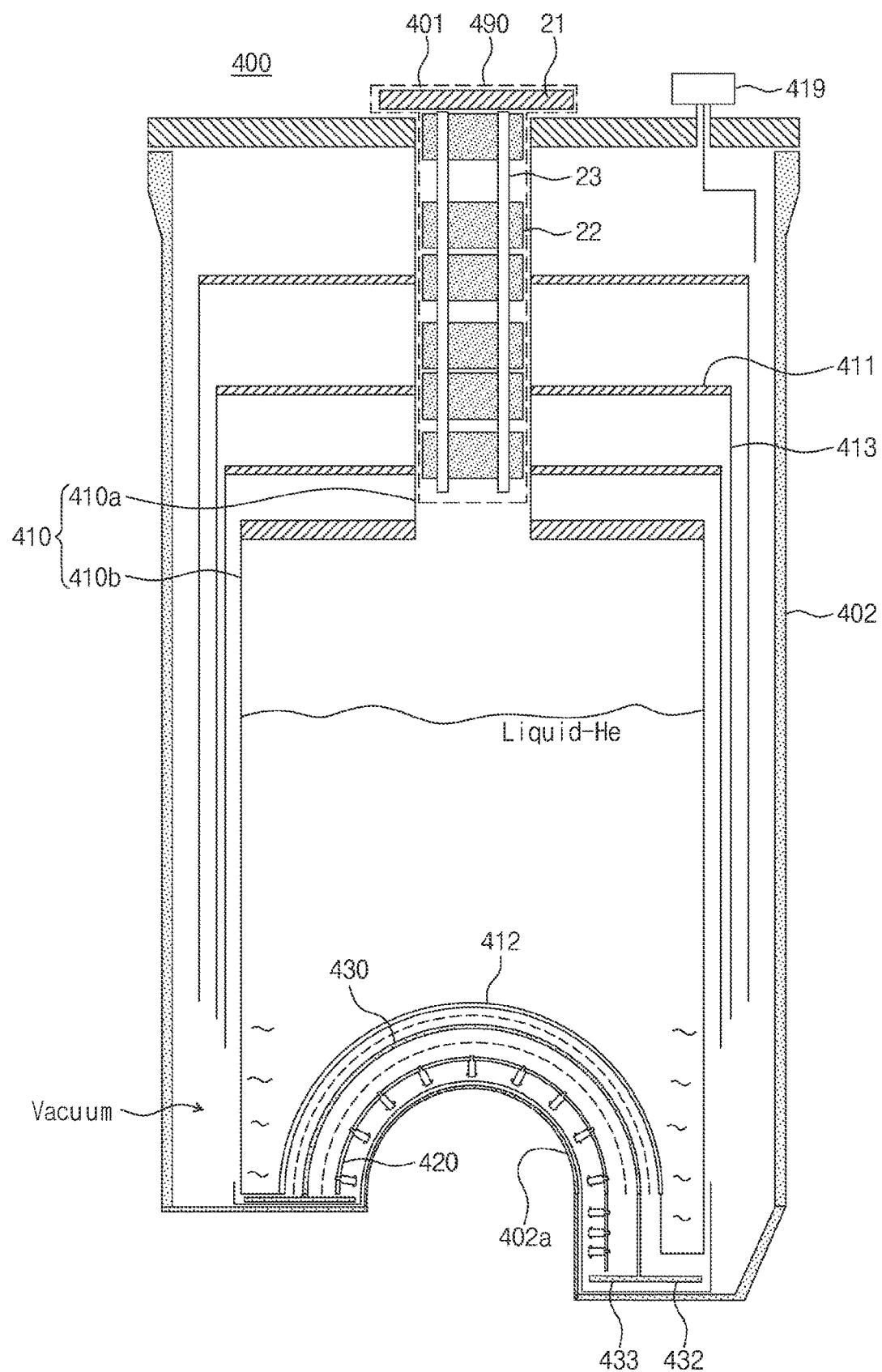
FIG. 8A illustrates an indirect cooling-type magnetoencephalography (MEG) measuring apparatus in which a magnetometer and a superconducting helmet shield are mounted in vacuum according to another example embodiment of the present disclosure.

FIG. 8A illustrates an indirect cooling-type magnetoencephalography (MEG) measuring apparatus in which a magnetometer and a superconducting helmet shield are mounted in vacuum according to another example embodiment of the present disclosure.

Figure 8B:
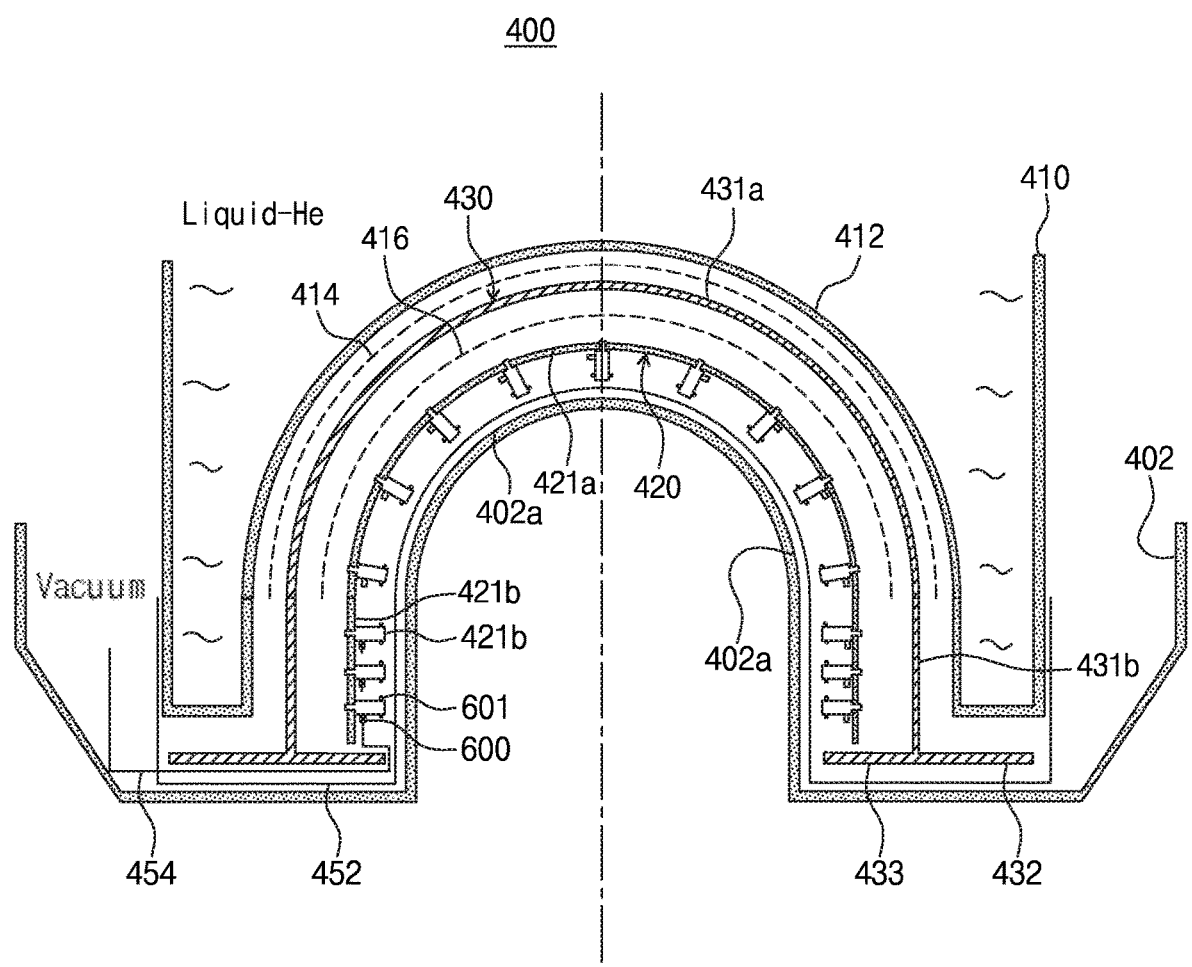
FIG. 8B is an enlarged cross-sectional view of the superconducting helmet in FIG. 8A.

FIG. 8B is an enlarged cross-sectional view of the superconducting helmet in FIG. 8A.

Figure 8C:
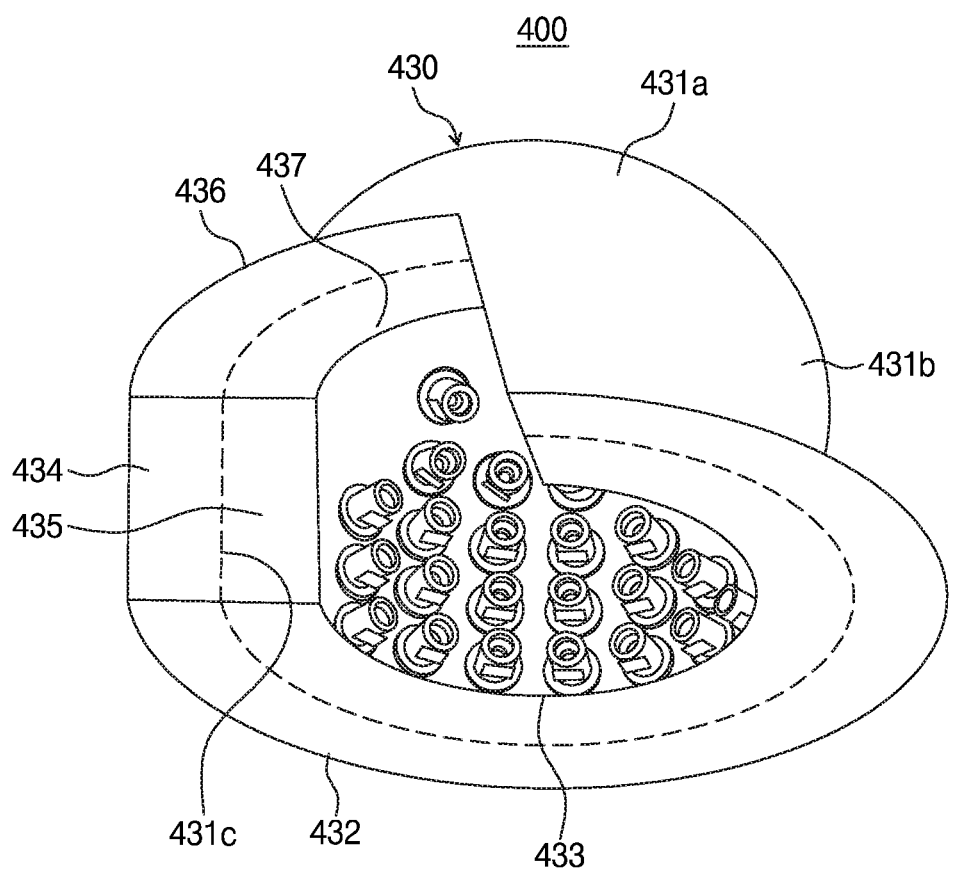
FIG. 8C is a perspective view of the superconducting helmet in FIG. 8A.

FIG. 8C is a perspective view of the superconducting helmet in FIG. 8A.

Figure 8D:
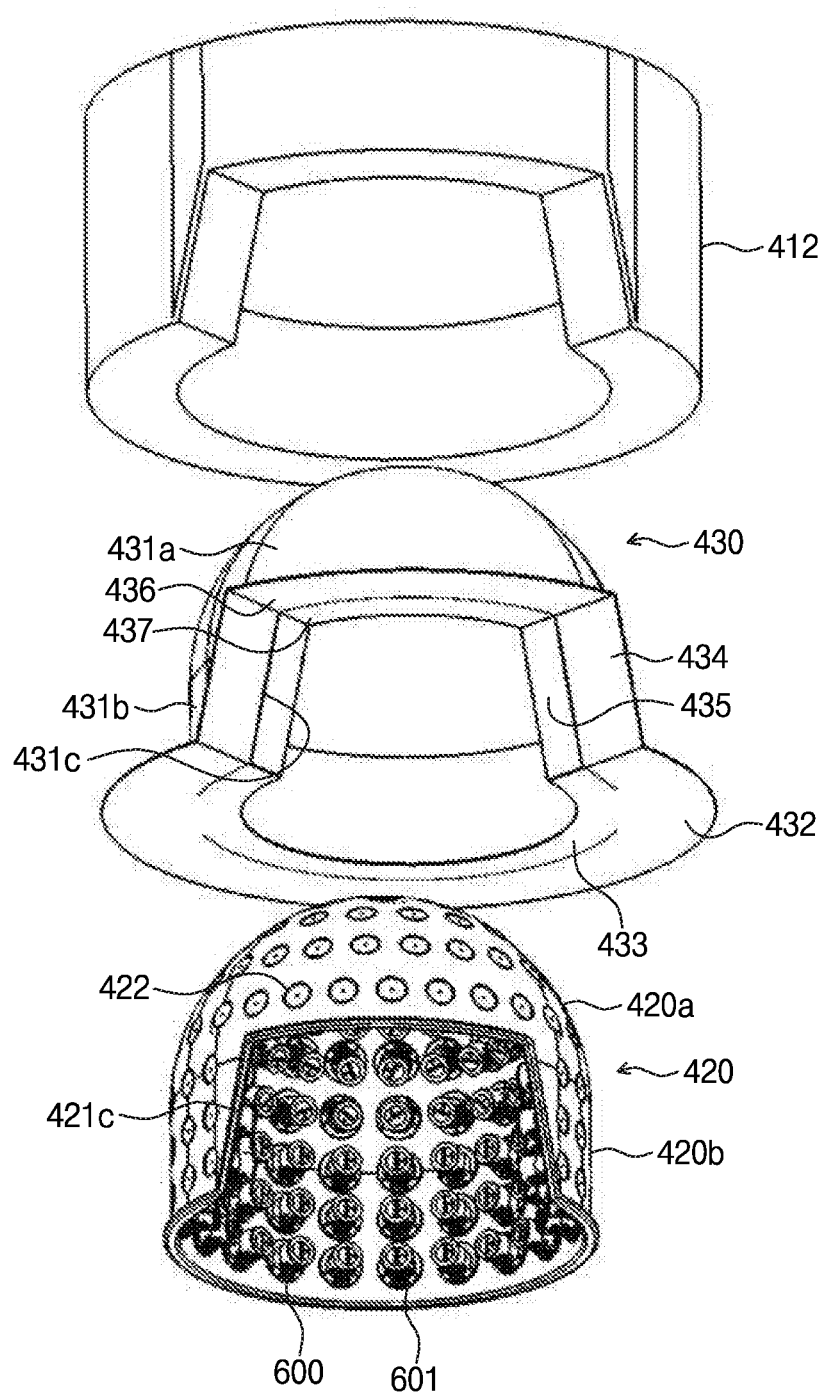
FIG. 8D is an exploded perspective view of the superconducting helmet in FIG. 8A.

FIG. 8D is an exploded perspective view of the superconducting helmet in FIG. 8A.

Referring to FIGS. 8A through 8D, a magnetoencephalography (MEG) measuring apparatus 400 may include an inner container 410 storing a liquid refrigerant and including an inner helmet 412, an outer container 402 including an outer helmet 402a disposed to cover the inner helmet 412, a sensor-mounted helmet 420 disposed in a space between the inner helmet 412 and the outer helmet 402a, and a superconducting quantum interference device (SQUID) sensor module 600 disposed in a space between the sensor-mounted helmet 420 and the outer helmet 402a and mounted on the sensor-mounted helmet 420.

The MEG measuring apparatus 400 may include the outer container 402, the inner container 410 disposed inside the outer container 402, and an insert 401 inserted into the inner container 410. The inside of the inner container 410 may be filled with a liquid refrigerant.

The MEG measuring apparatus 400 includes a superconducting helmet 430 having an inward brim and an outward brim, the sensor-mounted helmet 420 disposed in a space between the superconducting helmet 430 and the outer helmet 402a, and a SQUID sensor module disposed in a space between the sensor-mounted helmet 420 and the outer helmet 402a.

The SQUID sensor module 600 includes a pick-up coil 601 and a SQUID sensor 646 mounted on the sensor-mounted helmet 420 and connected to the pick-up coil 601.

A Dewar may include an outer container 402 and an inner container 410. The Dewar may have a coaxial cylindrical structure. A space between the outer container 402 and the inner container 410 is maintained in a vacuum state. The inner container 410 may include a top plate. A through-hole may be formed in the center of the top plate. The outer container 402 may be in the form of a cylinder. The outer helmet 402a may be disposed on a bottom surface of the outer container 402 to allow a person's head to be inserted.

The inner container 410 may include a neck portion 410a having a small diameter and a body portion 410b having a large diameter. The neck portion 410a and the body portion 410b may be in the form of a cylinder. An inner helmet 412 aligned with the outer helmet 402a may be disposed on a bottom surface of the body portion 410b.

A washer-shaped support portion 411 may be disposed on an outside surface of the neck portion 410a of the inner container 410. A thermal shielding portion 413 may be disposed on an outer circumferential surface of the support portion 411. The thermal shielding portion 413 may include an upper cylindrical portion and a lower slit portion continuously combined with the upper cylindrical portion. The lower slit portion may have a slit formed in a vertical direction. The thermal shielding portion 413 may be made of a conductive material. A liquid refrigerant may be stored in the inner container 410. The thermal shielding portion 413 may include multiple layers to reduce a temperature gradient in vacuum. The thermal shielding layer 413 may include an aluminum-coated Mylar layer and a copper layer that are sequentially stacked to block radiant heat. The thermal shielding portion 413 may block introduction of external radiant heat.

An insert 401 may be inserted into the neck portion 410*a* of the inner container 410 to perform an adiabatic function. The insert 401 may include an insert top plate 21, a guide rod 23 combined with the insert top plate 21 and extending vertically, and an insert baffle 22 inserted into the guide rod 23.

The insert top plate 21 may be in the form of a disc and be made of G-10 epoxy. The insert top plate 21 may be fixed to a top plate of the outer container 410.

The guide rod 23 may be made of G-10 epoxy and be in the form of a rod or a pipe. The guide rod 23 may be means or structure for supporting the insert baffle 22.

The insert baffle 22 may include Styrofoam with superior warmth retention and a conductive plate. The conductive plate may include an aluminum-coated Mylar layer and a copper layer. The insert baffle 12 may block external thermal conductivity and influx of radiant heat.

A space between the inner container 410 and the outer container may be maintained in a vacuum state. The sensor-mounted helmet 420 and the superconducting helmet 430 disposed on the sensor-mounted helmet 420 may be disposed between the outer helmet 402*a* and the inner helmet 412. Thus, the outer helmet 402*a*, the sensor-mounted helmet 420, the superconducting helmet 430, and the inner helmet 412 may be sequentially disposed. The inner helmet 412 may fix and cool the sensor-mounted helmet 420.

A connector box 419 electrically connects the SQUID sensor 442 to an external circuit. The connector box 419 may connect a wiring extending through a vacuum portion to the external circuit and be disposed on a top plate of the inner container 410.

The sensor-mounted helmet 420 includes a spherical portion 421*a* and a cylindrical straight portion 421*b* continuously connected to the spherical portion 421*a*. The straight portion 421*b* may be partially removed in a direction that a person's eye views. A plurality of through-holes 422 may be formed at the straight portion 421*b* and the hemispherical portion 421*a* of the sensor-mounted helmet 420. A SQUID sensor 442 is mounted in the through-hole 422.

The sensor-mounted helmet 420 may be made of G-10 epoxy and be fabricated with a plurality of components using an epoxy adhesive. The hemispherical portion 321*a* may have a hemispherical shape. The shape of the hemispherical portion 421*a* may be variously modified into, for example, a parabolic shape or an elliptical shape allowing a person's head to be inserted. The straight portion 421*b* may be continuously connected to the hemispherical portion 421*a*. Accordingly, the straight portion 421*b* may have a cylindrical shape. An azimuthal element of the straight portion 421*b* may be partially removed to provide a visual field ensuring portion 431*c*. Specifically, an azimuthal element having the range between 45 and 180 degrees may be removed. Thus, a person's eye may ensure a visual field when the person's head is inside the sensor-mounted helmet 420.

The superconducting helmet 430 includes an inward brim 433, an outward brim 432, a hemispherical portion 431*a*, a cylindrical straight portion 431*b* continuously connected to the hemispherical portion 431*a*, and a visual field ensuring portion 431*c* formed by partially removing the straight portion 431*b*. The superconducting helmet 430 may further include an inward side brim 435 disposed at opposite sides of the visual field ensuring portion 431*c* and connected to the inward brim 433, an outward side brim 434 disposed at opposite sides of the visual field ensuring portion 431*c* and connected to the outward brim 432, an inward upper brim 437 disposed on the visual field ensuring portion 431*c* and connected to the inward side brim 435, and an outward upper brim 436 disposed on the visual field ensuring portion 431*c* and connected to the outward side brim 334. The superconducting helmet 430 may shield external magnetic noise.

The inward brim 433, the inward side brim 435, and the inward upper brim 437 may be continuously connected. The outward brim 432, the outward side brim 434, and the outward upper brim 436 may be continuously connected. Length or width of the inward brim 433 may be 20 to 40 mm. Length or width of the outward brim 432 may be 40 to 60 mm. A material of the superconducting helmet 430 may be lead (Pb). The superconducting helmet 430 may be fabricated by folding a plate. The superconducting helmet 430 may be formed using a mold. A vertically spaced distance between a surface of the superconducting helmet 430 and the pick-up coil 441 may be 20 to 40 mm. The vertically spaced distance may be equal to the length of the inward brim 433. In this case, an MEG signal generated at an auditory cortex and a visual cortex may be measured.

A first thermal conduction layer 414 may be disposed between the inner helmet 412 and the superconducting helmet 430 to transfer heat between the inner helmet 412 and the superconducting helmet 430. Thus, the superconducting helmet 430 may be cooled to a low temperature. A second thermal conduction layer 416 may be disposed between the superconducting helmet 430 and the sensor-mounted helmet 420 to transfer heat between the superconducting helmet 430 and the sensor-mounted helmet 420. Thus, the sensor-mounted helmet 420 and the SQUID sensor module 440 may be cooled to a low temperature. The first thermal conduction layer 414 and the second thermal conduction layer 416 may be made of a conductive mesh.

A thermal cap 452 may be made of a material having high thermal conductivity and increase cooling efficiency of the sensor module 440. The thermal cap 452 may be disposed between the sensor-mounted helmet 420 and the outer container 402. The thermal cap 452 may be disposed to cover the sensor-mounted helmet 420. The thermal cap 452 may be thermally connected to the lower end of a body portion 410*b* of the inner container 410. The thermal cap 452 may be a copper mesh for thermal conduction and an aluminum-coated thin Mylar material for thermal reflection.

The superconducting quantum interference device (SQUID) sensor module 600 may include a fixed block 610 having one end fixed to a supporting part 50, a bobbin 630 having one end combined with the other end of the fixed block 610 and a groove in which a pick-up coil 601 is wound, a bobbin fixing or attachment structure or material 650 fixed to the other end of the fixed block 610 via a through-hole formed in the center of the bobbin 630, a SQUID printed circuit board (PCB) 640 disposed on an upper side surface of the bobbin 630 and including a SQUID sensor 646, and a signal line connection PCB 620 inserted into an outer circumferential surface of the fixed block 610 and adapted to transmit a signal detected in the SQUID sensor 646 to an external circuit.

Eight strands of power and signal line connected from the connector box 419 are formed at the connection line PCB 2.

One hundred or more SQUID sensor modules are used to measure and analyze an MEG signal. The SQUID sensor modules are maintained at optimal intervals to avoid duplication of signal detection.

A CIV-type Dewar may dramatically decrease a sectional area of a Dewar neck, as compared to a direct cooling type Dewar where a SQUID is submerged in liquid helium to be cooled. Thus, the CIV-type Dewar may significantly reduce consumption of a high-priced low-temperature refrigerant. However, when a first-order gradiometer SQUID sensor is used, a heat influx area in a helmet is significantly widened to increase an evaporation rate of the low-temperature refrigerant.

To overcome the above disadvantage, a superconducting helmet and a SQUID sensor module having a compact structure were used in a CIV-type MEG. When a SQUID magnetometer is shielded with a superconductor, the SQUID magnetometer may have the same operation characteristics as a SQUID gradiometer due to superconducting image current. If these characteristics are applied to a CIV-type MEG apparatus, a surface area of a vacuum vessel helmet where a SQUID sensor module is disposed may decrease by 40 percent. In addition, a surface area of a thermal shield layer exposed to an absolute temperature of 300 K may decrease by 290 percent as compared to a CIV-type MEG apparatus including a gradiometer. Thus, thermal leakage from a lower end of a low-temperature coolant storage container may be significantly reduced. Specifically, when the integrated magnetometer is used, a distance between an outer helmet and an inner helmet decreases as length of the bobbin decreases. On the other hand, an area of a bottom surface between the inner helmet and the outer helmet viewing a bottom surface of the external container maintained at room temperature decreases. As the area of the bottom surface decreases, thermal introduction through the area may be reduced to decrease a refrigerant evaporation rate.

A superconducting helmet having an inward brim allows an MEG signal generated at an auditory cortex and a visual cortex to be easily measured. Since the superconducting helmet having the inward brim may shield magnetic nose of all frequency bands, miniaturization and weight reduction of a magnetically shielded room may be achieved.

A superconducting shield according to the present disclosure was applied to a 152-channel MEG SQUID apparatus. An auditory evoked signal and a visual evoked signal were measured with respect to a normal person by using the MEG SQUID apparatus to which the present disclosure is applied. A signal-to-noise ratio (SNR) of the measured signal was improved five or more times as compared to a normal superconducting shield.

As described above, a SQUID sensor module according to an example embodiment of the present disclosure is provided with a compact structure to be mounted on a helmet-type MEG measuring apparatus and to improve spatial availability.

Although the present disclosure and its advantages have been described in detail, it should be understood that various changes, substitutions and alterations can be made herein without departing from the spirit and scope of the disclosure as defined by the following claims.

What is claimed is:

1. A superconducting quantum interference device (SQUID) sensor module comprising:
    a fixed block having one end fixed to a supporting part;
    a bobbin having one end combined with another end of the fixed block and a groove in which a pick-up coil is wound;
    a bobbin fixing structure fixed to the other end of the fixed block via a through-hole formed in the center of the bobbin;
    a SQUID printed circuit board (PCB) disposed on an upper side surface of the bobbin and including a SQUID sensor; and
    a signal line connection PCB inserted into an outer circumferential surface of the fixed block and adapted to transmit a signal detected in the SQUID sensor to an external circuit.

2. The superconducting quantum interference device (SQUID) sensor module as set forth in claim 1, wherein the signal line connection PCB includes a first connector,
    the SQUID printed circuit board (PCB) includes a second connector, and
    the first connector and the second connector are electrically connected to each other.

3. The superconducting quantum interference device (SQUID) sensor module as set forth in claim 1, wherein the fixed block comprises:
    a fixed block protruding portion having a disc shape and combined with a groove or a through-hole formed at the supporting part;
    a fixed block threshold portion having a disc shape, continuously connected to the fixed block protruding portion, and having a flat side surface having a larger diameter than the fixed block protruding portion;
    a fixed block body portion having a disc shape, continuously connected to the fixed block threshold portion, and having a flat side surface having a smaller diameter than the fixed block threshold portion; and
    a fixed block extending portion having a diameter equal to that of the fixed block body portion and having a flat side surface,
    wherein the flat side surface of the fixed block threshold portion and the flat side surface of the fixed block body portion are connected to each other,
    one side surface of the fixed block body portion and one side surface of the fixed block extending portion are parallel to each other, and
    a vertical distance between a central shaft and one side surface of the fixed block extending portion is smaller than a vertical distance between the central shaft and one side surface of the fixed block body portion.

4. The superconducting quantum interference device (SQUID) sensor module as set forth in claim 3, further comprising:
    a connection line electrically connecting the pick-up coil and the SQUID sensor to each other,
    wherein opposite ends of the pick-up coil are fixed to the second flat portion, and
    the connection line electrically connects a conductive pad of the SQUID sensor and the opposite ends of the pick-up coil to each other.

5. The superconducting quantum interference device (SQUID) sensor module as set forth in claim 1, wherein the bobbin comprises:
    a first flat portion having a first vertical distance from a central shaft and formed on an upper side surface; and
    a second flat portion having a second vertical distance greater than the first vertical distance and formed on a lower side surface.

6. The superconducting quantum interference device (SQUID) sensor module as set forth in claim 1, wherein the signal line connection PCB is in the form of a washer having a through-hole formed therein, and one side surface of the through-hole is a plane to prevent a rotational motion when the signal line connection PCB is combined with an outer circumferential surface of the fixed block.

7. The superconducting quantum interference device (SQUID) sensor module as set forth in claim 1, wherein the pick-up coil is a first-order gradiometer or a magnetometer.

\* \* \* \* \*